United States Patent [19]
Akashi et al.

[11] Patent Number: 6,100,338
[45] Date of Patent: Aug. 8, 2000

[54] FINE GRAIN CARRIERS AND MEDICINAL COMPOSITION PREPARED WITH THE USE OF THE SAME

[75] Inventors: Mitsuru Akashi; Akio Kishida, both of Kagoshima; Shinji Sakuma; Hiroshi Kikuchi, both of Tokyo, all of Japan

[73] Assignee: Daiichi Pharmaceutical Co., Ltd., Tokyo, Japan

[21] Appl. No.: 09/101,804

[22] PCT Filed: Feb. 20, 1997

[86] PCT No.: PCT/JP97/00463

§ 371 Date: Aug. 21, 1998

§ 102(e) Date: Aug. 21, 1998

[87] PCT Pub. No.: WO97/30730

PCT Pub. Date: Aug. 28, 1997

[30] Foreign Application Priority Data

Feb. 21, 1996 [JP] Japan ................................. 8-033200
May 21, 1996 [JP] Japan ................................. 8-126137

[51] Int. Cl.$^7$ ............................... A61K 9/14; A61K 47/30
[52] U.S. Cl. .......................... 525/212; 525/217; 525/227; 525/230; 526/286; 526/304; 526/307.6; 526/307.7; 427/213.34
[58] Field of Search ............................ 525/78, 925, 212, 525/218, 221, 222, 217, 227, 230; 526/286, 288, 307.6, 307.7, 304

[56] References Cited

U.S. PATENT DOCUMENTS

| | | | |
|---|---|---|---|
| 2,811,507 | 10/1957 | D'Alelio | 526/304 |
| 4,008,202 | 2/1977 | Evani et al. | 526/304 |
| 4,011,201 | 3/1977 | Ponticello | 526/307.7 |
| 5,061,761 | 10/1991 | Sato et al. | 525/329.8 |
| 5,250,629 | 10/1993 | Tani et al. | 125/268 |

OTHER PUBLICATIONS

Chem. Ab. vol. 123:286978 H.–O. Kim et al, Apr. 1993.
C.Ab. 125:143400, Feb. 1996.
C.Ab. 125:59765, Jan. 1995.

*Primary Examiner*—Peter F. Kulkosky
*Attorney, Agent, or Firm*—Oblon, Spivak, McClelland, Maier & Neustadt, P.C.

[57] ABSTRACT

The present invention is directed to particulate carriers useful as drug carries in a drug delivery system (DDS) and to pharmaceutical compositions making use of such carriers. The invention is characterized by the use, as the particulate carrier, of: graft copolymer (A) whose graft chain is poly N-alkylacrylamide chain, poly N-alkylmethacrylamide chain, etc.; and composition containing a combination of the graft copolymer (A) and at least one graft copolymer selected from the group consisting of graft copolymers (B-1) having polyacrylic acid or polymethacrylic acid as the graft chain and graft copolymers (B-2) having a polyvinyl amine compound as the graft chain.

2 Claims, 11 Drawing Sheets

FINE GRAIN CARRIERS AND MEDICINAL COMPOSITION PREPARED WITH THE USE OF THE SAME

TECHNICAL FIELD

The present invention relates to particulate carriers which are useful as drug carriers in a drug delivery system (DDS) and to pharmaceutical compositions containing the carriers.

BACKGROUND ART

In the field of DDS, the term "drug carriers" is used to refer to carriers that deliver drugs to target organs or cells. When drug carriers are in the form of particles, they are called particulate carriers. Particulate carriers are classified into microcapsules, microspheres, nanoparticles, etc. according to their sizes, shapes, and functions. Materials for preparing particulate carriers include lipids, polymers, etc.

The terms "microcapsules" and "microspheres" are usually used to refer to particles whose diameter is several micrometers. Microcapsules are generally considered to embrace a broader category than microspheres. Particles formed of a polymer from the surface to the core are often distinguished from microcapsules and are referred to as microspheres these days.

The term "nanoparticles" has conventionally been used to refer to polymeric colloids prepared through emulsion polymerization, as the particles size is on the order of several nanometers. However, it has recently become common practice to collectively refer to particles composed of natural or synthetic polymers, even though prepared through methods other than emulsion polymerization, as nanoparticles so long as the particle diameter is on the order of several nanometers.

Nanoparticles as particulate carriers were first studied for use as carriers for targeting, for example, anti-cancer agents. In the early studies, the primary object of application was injection (L. Grislain et al., International Journal of Pharmaceutics, 15, 335 (1984)). Since the mid 1980's, studies of nanoparticles as oral dosage forms have come to be reported.

When drugs are prepared as the form of nanoparticles and used as oral dosage forms, the following are considered goals to attain: improvement of drugs with poor absorptive characteristic (P. Maincent et al., Journal of Pharmaceutical Sciences, 75, 955 (1986); C. Damge et al., International Journal of Pharmaceutics, 36, 121 (1987)), oral dosage forms of peptide drugs such as insulin (C. Damge et al., Diabetes, 37, 246 (1988); P. Couvreur and F. Puisieux, Advanced Drug Delivery Reviews, 10, 141 (1993)), oral delivery of vaccines antigen (J. H. Eldrige, Journal of Controlled Release, 11, 205 (1990)t; P. U. Jani et al., International Journal of Pharmaceutics, 86, 239 (1992)), and controlled release of drugs (B. Hubert et al., Pharmaceutical Research, 8, 734 (1991)).

Moreover, like the case of microcapsules, nanoparticles are sometimes used in an attempt to ensure stability of drugs in gastrointestinal tract (M. Rogues et al., Diabetes, 41, 451 (1992)) or to reduce irritation caused by strongly stimulative drugs on gastrointestinal mucosa (N. Ammoury et al., Pharmaceutical Research, 8, 101 (1991)).

Nanoparticles for pharmaceutical use are principally prepared by one of the two methods. The first method is a typical microcapsulation method, which is practiced through phase separation or solvent evaporation.

When this method is practiced, there are usually used hydrophobic polymers that have customarily been used as additives for pharmaceuticals, such as polylactic acid (A. M. Ray et al., Journal of Pharmaceutical Sciences, 83, 845 (1994)), cellulose derivatives (H. Ibrahim et al., International Journal of Pharmaceutics, 87, 239 (1992), or polyacrylate derivatives (E. Allemann et al., International Journal of Pharmaceutics, 87, 247 (1992)).

The other method for the preparation of nanoparticles makes use of emulsion polymerization (L. Vansnick et al., Pharmaceutical Research, 1, 36 (1985); N. Al Khouri Fallouh et al., International Journal of Pharmaceutics, 28, 125 (1986)). In this case, hydrophobic polyvinyl compounds such as polystyrene, polyacrylate, and polymethacrylate are considered to serve as the material of the nanoparticles. Polycyanoacrylates are used quite often, especially polyisobutyl cyanoacrylate, which is an adhesive for surgical operations.

Drug products are prepared by combining a drug with nanoparticles so as to carry the drug. Drugs to be carried are usually hydrophobic compounds, because the method for prepareg nanoparticles is not suitable for hydrophilic compounds. Although there have been reported some examples in which hydrophilic compounds are transformed into nanoparticles, they are in effect limited to only compounds (e.g., peptides) that are insoluble in water at a certain pH (Yoshiaki KAWASHIMA, The 114th Conference of Japan Pharmaceutical Society, Lecture Abstracts Vol. 4, page 9, 1994, Tokyo).

Examples of studies in which the thus-prepared nanoparticle-drug complexes are used so as to improve absorption of poor absorptive drugs, to prepare oral dosage forms of peptide drugs, and to control the release of drugs include the following.

P. Maincent et al. prepared nanoparticles of vincamine, a poor absorptive hypotensive drug, through use of polyhexyl cyanoacrylate and studied absorption enhancement effect. However, the absorption rate of vincamine after transformation into nanoparticles was only 1.6 times that before transformation (Journal of Pharmaceutical Sciences, 75, 955 (1986)).

C. Damge attempted to prepare oral dosage forms of peptides by encapsulating insulin into nanoparticles through use of polyisobutyl cyanoacrylate. However, a slight decrease in blood glucose was observed only when nanoparticles containing a considerable amount of insulin were administered perorally, under fasting, to rats that had experimentally induced diabetes (Diabetes, 37, 246 (1988)).

Moreover, B. Hubert et al. studied controlled release of drugs using darodipine, a hypotensive drug. However, they were successful only in reducing initial release of the drug by encapsulating the drug into nanoparticles (Pharmaceutical Research, 8, 734 (1991)). There is no report that controlled release was acheived by nanoparticles.

As described above, there was no particulate carriers that have the sufficient oral absorption enhancement effect of drugs. Accordingly, the present invention is directed to a particulate carrier that has an excellent enhancement effect of drug absorption, and also to a pharmaceutical composition containing the carrier.

DISCLOSURE OF THE INVENTION

The present inventors conducted extensive studies, focusing on graft copolymers as drug carriers particularly the absorption enhancement of drugs administered orally. They found that graft copolymers having graft chains composed of polyvinylamine compound show an excellent oral absorption enhancement effect, and filed a pertinent patent application (Japanese Patent Application Laid-Open (kokai) No. 8-268916). After continued studies, they unexpectedly found that combinations of one or more species of graft copolymers having the graft chains composed of poly N-alkylacrylamide or poly N-alkylmethacrylamide shown below exhibit a remarkably superior oral absorption enhancement effect as compared to conventional graft copolymers, leading to completion of the present invention.

Accordingly, the present invention provides a particulate carrier including a graft copolymer (A) having structural units of the following formulae (1) and (2):

(1)

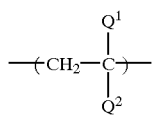

wherein
$Q^1$ is a hydrogen atom, a methyl group, or a cyano group, and
$Q^2$ is a hydrogen atom,

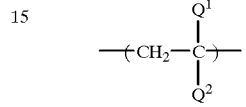

wherein
$R^1$ is a hydrogen atom or a halogenomethyl group,
$R^2$ is a $C_1$–$C_{10}$ alkyl group,
$R^3$ is a hydrogen atom or a $C_1$–$C_{10}$ alkyl group, and
$R^4$ is a $C_1$–$C_{10}$ alkyl group, provided that the carbon number in total of $R^3$ and $R^4$ is between 3 and 20 inclusive;

(2)

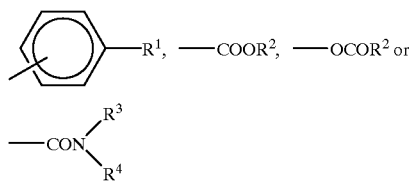

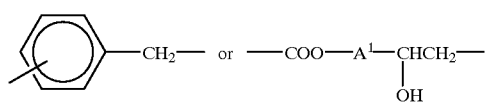

wherein
$Q^3$ is a hydrogen atom or a methyl group,
$Q^4$ is a group having the following structure:

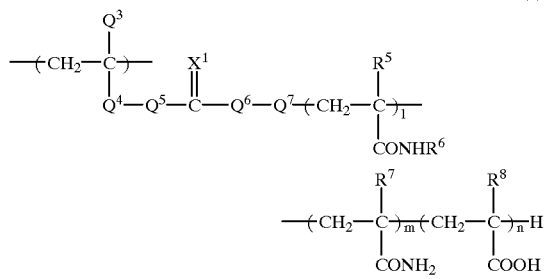

wherein A1 is a $C_1$–$C_{10}$ alkylene group,
$Q^5$ is an oxygen atom or —NH—,
$Q^6$ is a $C_1$–$C_{10}$ alkylene group,
$Q^7$ is an oxygen atom or a sulfur atom,
$X^1$ is an oxygen atom or two hydrogen atoms, each of $R^5$, $R^7$, and $R^8$ is a hydrogen atom or a methyl group, $R^6$ is a $C_1$–$C_{10}$ alkyl group,
1 is a number from 1 to 100, and each of m and n is a number from 0 to 100.

The present invention also provides a particulate carrier composition containing a composition (graft copolymer composition) of the following components (a) and (b):
(a) the aforementioned graft copolymer (A); and
(b) one or more graft copolymers selected from the group consisting of the following graft copolymers (B-1) and (B-2):
(B-1) a graft copolymer having structural units of the following formulae (1) and (3):

(1)

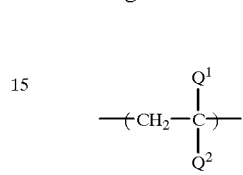

wherein
$Q^1$ is a hydrogen atom, a methyl group, or a cyano group, and
$Q^2$ is a hydrogen atom,

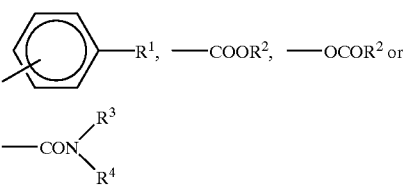

wherein
$R^1$ is a hydrogen atom or a halogenomethyl group,
$R^2$ is a $C_1$–$C_{10}$ alkyl group,
$R^3$ is a hydrogen atom or a $C_1$–$C_{10}$ alkyl group, and
$R^4$ is a $C_1$–$C_{10}$ alkyl group, provided that the carbon number in total of $R^3$ and $R^4$ is between 3 and 20 inclusive;

(3)

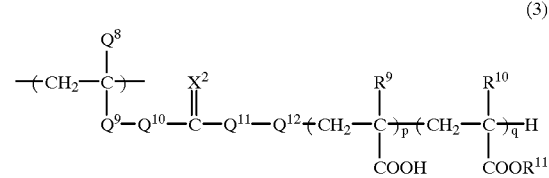

wherein
$Q^8$ is a hydrogen atom or a methyl group,
$Q^9$ is a group having the following structure:

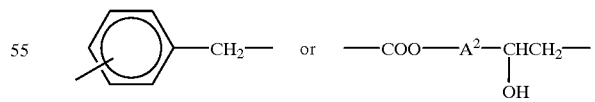

wherein $A^2$ is a $C_1$–$C_{10}$ alkylene group,
$Q^{10}$ is an oxygen atom or —NH—,
$Q^{11}$ is a $C_1$–$C_{10}$ alkylene group,
$Q^{12}$ is an oxygen atom or a sulfur atom,
$X^2$ is an oxygen atom or two hydrogen atoms, each of $R^9$, and $R^{10}$ is a hydrogen atom or a methyl group,
$R^{11}$ is a $C_1$–$C_{10}$ alkyl group, and
p and q are independently numbers from 0 to 100 such that the sum p+q is equal to or more than 1;

(B-2) a graft copolymer having structural units of the following formulae (1) and (4):

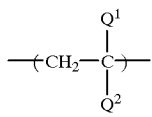
(1)

wherein
$Q^1$ is a hydrogen atom, a methyl group, or a cyano group, and
$Q^2$ is a hydrogen atom,

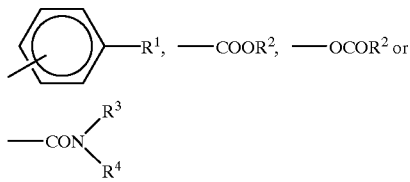

wherein
$R^1$ is a hydrogen atom or a halogenomethyl group,
$R^2$ is a $C_1$–$C_{10}$ alkyl group,
$R^3$ is a hydrogen atom or a $C_1$–$C_{10}$ alkyl group, and
$R^4$ is a $C_1$–$C_{10}$ alkyl group, provided that the carbon number in total of $R^3$ and $R^4$ is between 3 and 20 inclusive;

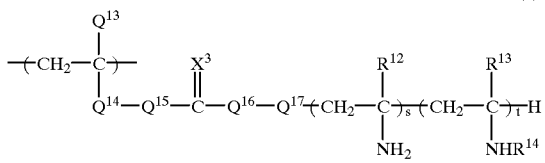
(4)

wherein
$Q^{13}$ is a hydrogen atom or a methyl group,
$Q^{14}$ is a group having the following structure:

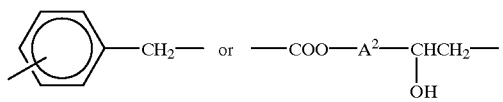

wherein $A^3$ is a $C_1$–$C_{10}$ alkylene group,
$Q^{15}$ is an oxygen atom or —NH—,
$Q^{16}$ is a $C_1$–$C_{10}$ alkylene group,
$Q^{17}$ is an oxygen atom or a sulfur atom,
$X^3$ is an oxygen atom or two hydrogen atoms, each of $R^{12}$ and $R^{13}$ is a hydrogen atom or a methyl group,
$R^{14}$ is a $C_2$–Cl, alkanoyl group, and s and t are independently numbers from 0 to 100 such that the sum s+t is equal to or more than 1.

The present invention also provides a pharmaceutical composition containing a drug and the aforementioned graft copolymer (A), or a drug and the aforementioned graft copolymer composition containing the components (a) and (b).

BEST MODE FOR CARRYING OUT THE INVENTION

Figure 1A:
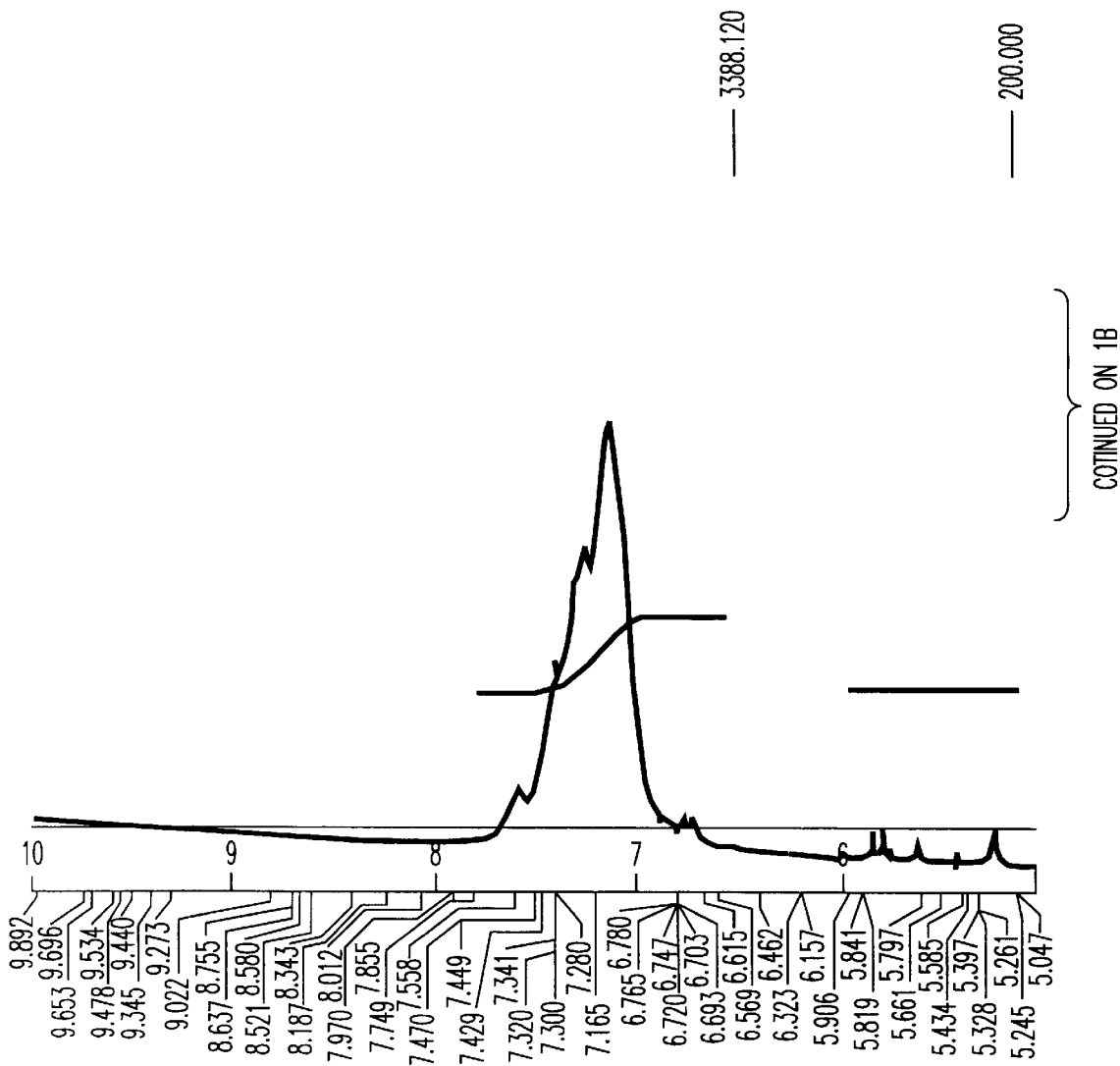
FIG. 1 is a proton NMR chart of the N-isopropylacrylamide macromonomer synthesized in Reference Example 1-2.

The graft copolymers which may be used in the particulate carriers and in the pharmaceutical compositions of the-present invention are categorized into the following three groups; namely, graft copolymers (A) having structural units (1) and (2), graft copolymers (B-1) having structural units (1) and (3), and graft copolymers (B-2) having structural units (1) and (4).

The proportion of graft chains present in these graft copolymers is not particularly limited. However, from the viewpoint of the enhancement effect of drug absorption, the mole fraction of the structural unit of formula (2), (3), or (4) should be between 0.001 and 1.

Next will be described the symbols used in formulae (1), (2), (3), and (4), which represent structural units composing of the graft copolymers of the present invention.

In formula (1), examples of the halogenomethyl groups represented by $R^1$ include a chloromethyl group, bromomethyl group, an iodomethyl group etc. The $C_1$–$C_{10}$ alkyl groups represented by $R^2$, $R^3$, and $R^4$ may be linear or branched; specific examples of which include a methyl group, ethyl group, n-propyl group, isopropyl group, n-butyl group, t-butyl group, n-pentyl group, n-hexyl group etc. Of these, $R^2$ is preferably $C_1$–$C_5$ alkyl, with a methyl group, ethyl group, and an isopropyl group being particularly preferred. There are two cases: one in which $R^3$ is a hydrogen atom and $R^4$ is an alkyl group, and one in which $R^3$ and $R^4$ are both alkyl groups. In either case, the carbon number in total is between 3 and 20 inclusive. For example, when $R^3$ is a hydrogen atom, $R^4$ is an alkyl group having 3–10 carbon atoms, and when $R^3$ and $R^4$ are both alkyl groups, $R^3$ and $R^4$ are alkyl groups such that the carbon number in total is between 3 and 20 inclusive.

Among the structural units represented by formula (1), the structural unit of the following formula (1a):

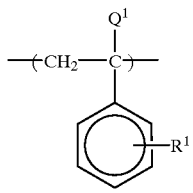

(1a)

(wherein $Q^1$ and $R^1$ have the same meanings as defined above) is preferred, and the structural unit of the following formula (1b):

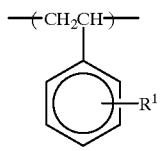

(1b)

(wherein $R^1$ has the same meaning as defined above) is particularly preferred.

In formulae (2), (3), and (4), the $C_1$–$C_{10}$ alkylene groups represented by $A^1$, $A^2$, $A^3$, $Q^6$, $Q^{11}$, and $Q^{16}$ may be linear or branched; specific examples of which include a methylene group, ethylene group, trimethylene group, hexamethylene group, propylene group, (ethyl)ethylene group, (dimethyl)ethylene group etc. Of these, $C_1$–$C_5$ linear or branched alkylene groups are preferred.

The $C_1$–$C_{10}$ alkyl groups represented by $R^6$ and $R^{11}$ may be linear or branched, specific examples of which include a methyl group, ethyl group, n-propyl group, isopropyl group, n-butyl group, t-butyl group, n-pentyl group, an n-hexyl group etc. Of these, $R^6$ is preferably $C_3$–$C_{10}$ branched alkyl groups, in which isopropyl groups are particularly preferred. $R^{11}$ is preferably $C_1$–$C_8$ linear or branched alkyl groups, in which a methyl group, ethyl group, isopropyl group, t-butyl group, and an n-hexyl group are particularly preferred.

The $C_2$–$C_{11}$ alkanoyl groups represented by $R^{14}$ may be linear or branched. Preferably, they have 2 to 6 carbon atoms. An acetyl group, propionyl group, and a butyryl group are particularly preferred.

In formula (2), because each of m and n may be zero, there are cases in which the structural unit of formula (2) takes the structure represented by one of the following formulae (2a), (2b), (2c) and (2d):

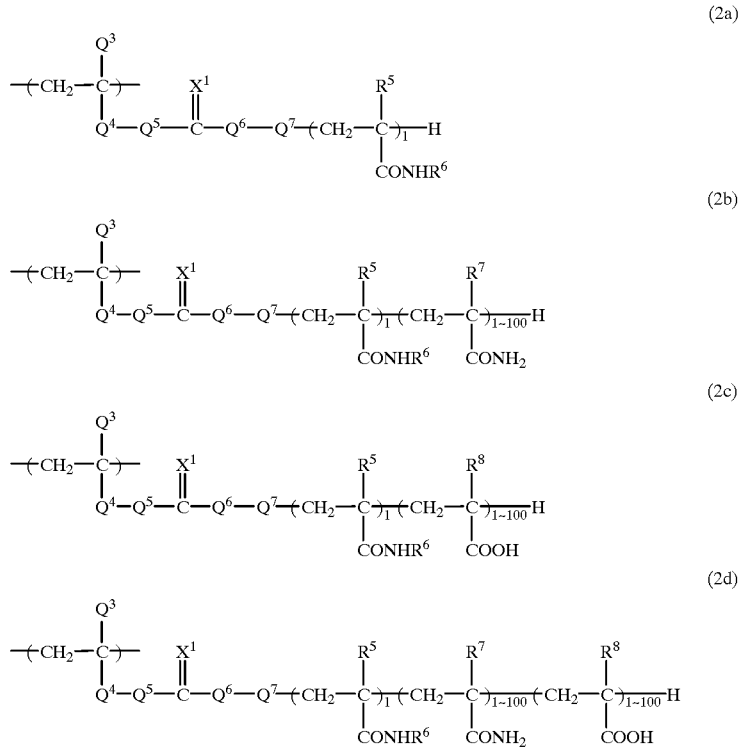

wherein $Q^3$, $Q^4$, $Q^5$, $Q^6$, $Q^7$, $X^1$, $R^5$, $R^6$, $R^7$, $R^8$, and l have the same meanings as defined above.

Of the structural units of formula (2), preferred are those of formula (2e):

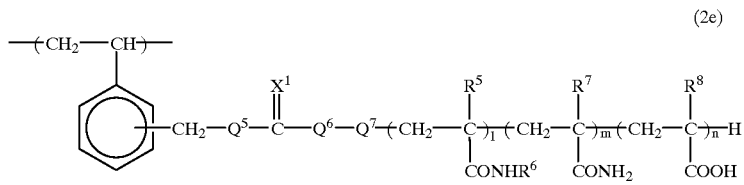
(2e)

(wherein $Q^5$, $Q^6$, $Q^7$, $X^1$, $R^5$, $R^6$, $R^7$, $R^8$, l, m, and n have the same meanings as defined above), and particularly preferred are those of formulae (2f) and (2g):

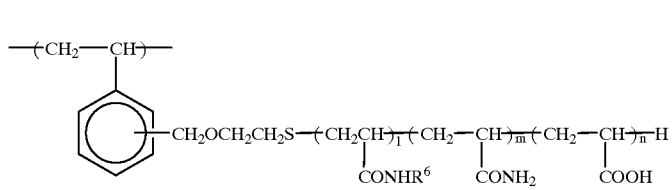
(2f)

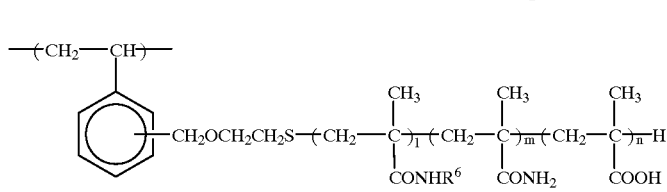
(2g)

(wherein $R^6$, l, m, and n have the same meanings as defined above).

In formula (3), because each of p and q may be zero, there are cases in which the structural unit of formula (3) takes the structure represented by one of the following formulae (3a), (3b), and (3c):

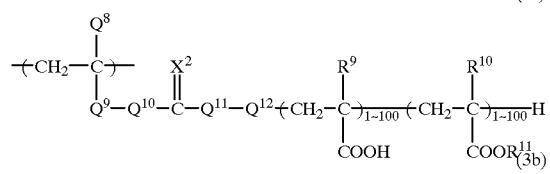
(3a)

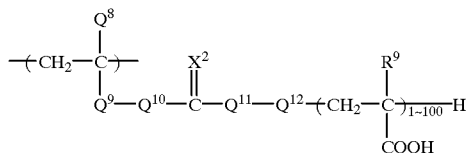
(3b)

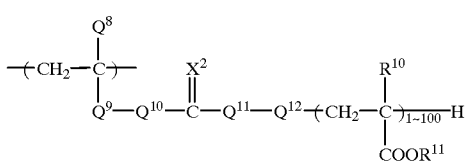
(3c)

wherein $Q^8$, $Q^9$, $Q^{10}$, $Q^{11}$, $Q^{12}$, $X^2$, $R^9$, $R^{10}$, and $R^{11}$ have the same meanings as defined above.

Of the structural units of formula (3), preferred are those of formula (3d):

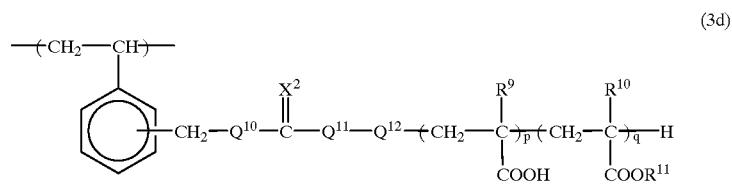
(3d)

(wherein $Q^{10}$, $Q^{11}$, $Q^{12}$, $X^2$, $R^9$, $R^{10}$, $R^{11}$, p, and q have the same meanings as defined above), and particularly preferred are those of formulae (3e) and (3f):

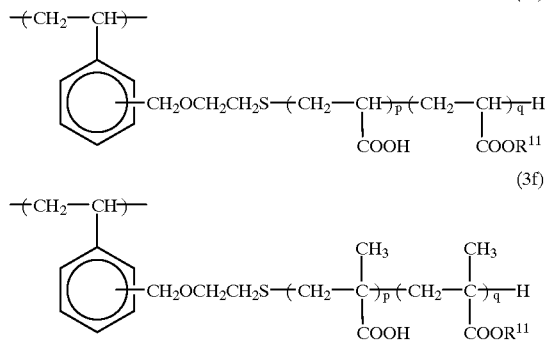

(wherein $R^{10}$, p, and q have the same meanings as defined above).

In formula (4), because each of s and t may be zero, there are cases in which the structural unit of formula (4) takes the structure represented by one of the following formulae (4a), (4b), (4c):

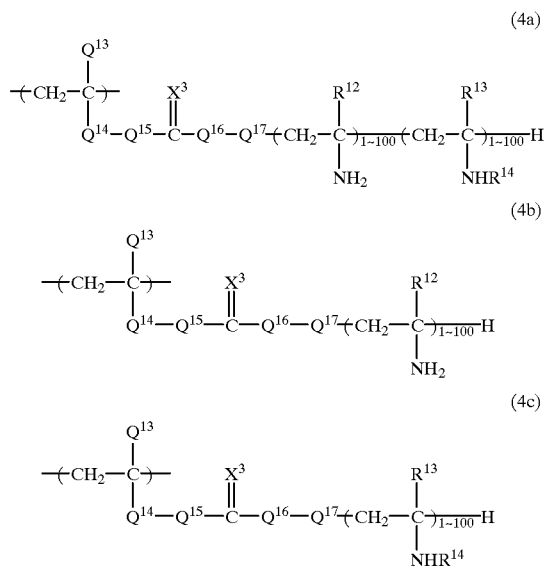

wherein $Q^{13}$, $Q^{14}$, $Q^{15}$, $Q^{16}$, $Q^{17}$, $X^3$, $R^{12}$, $R^{13}$, and $R^{14}$ have the same meanings as defined above.

Of the structural units of formula (4), preferred are those of formula (4d):

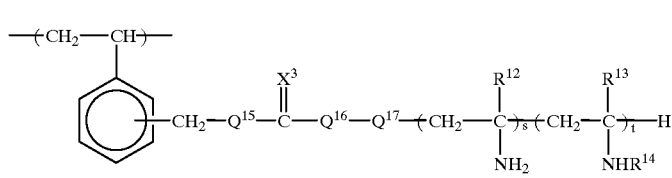

(wherein $Q^{15}$, $Q^{16}$, $Q^{17}$, $X^3$, $R^{12}$, $R^{13}$, $R^{14}$, s, and t have the same meanings as defined above), and particularly preferred are those of formulae (4e) and (4f):

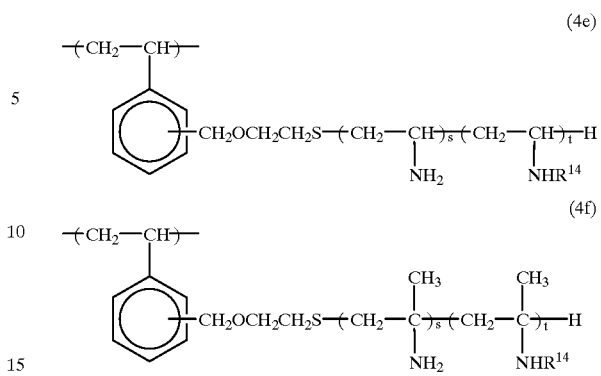

(wherein $R^{13}$, s, and t have the same meanings as defined above).

In the above-described graft copolymers, the recurring unit in each graft chain (such as N-alkylacrylamide, N-alkylmethacrylamide, acrylamide, methacrylamide, acrylic acid, vinylamine, N-alkanoylvinylamine etc.) may be of the random type or the block type. Also, bonding between the structural unit of formula (1) and the structural unit of any one of formula (2), (3), or (4) may be of the random type or the block type.

Of the aforementioned graft copolymers of formula (A), those falling within the following three categories are novel: graft copolymers composing of structural units of formula (1) and formula (2b); graft copolymers composing of structural units of formula (1) and formula (2c); and graft copolymers composing of structural units of formula (1) and formula (2d).

The graft copolymers may be prepared by, for example, synthesizing a macromonomer corresponding to the structural unit of formula (2), (3), or (4), and subsequently copolymerizing the resultant macromonomer and a vinyl compound that corresponds to formula (1).

The method for preparing the graft copolymers will next be described in detail.

A macromonomer which corresponds to the structural unit of formula (2), (3), or (4) may be readily prepared through radical polymerization, in the presence of a chain transfer agent having an amino group, a hydroxyl group, or a carboxyl group in the molecule, of one or more monomers (for example, an alkylacrylamide derivative, and an alkylmethacrylamide derivative) corresponding to the recurring unit of any one of the formulae (2) through (4), to thereby synthesize one or more polymers or copolymers each having an amino, hydroxyl, or carboxyl group (for example, polymer s or copolymers of an alkylacrylamide derivative or an alkylmethacrylamide derivative) in the terminal, and subsequently reacting the resultant polymers or copolymers with a vinyl monomer such as vinyl benzyl halide or alkyl methacrylate dioxide.

Polymerization of one or more monomers such as an alkylacrylamide derivative or an alkylmethacrylamide derivative is performed in the presence of a chain transfer agent and a radical polymerization initiator. During polymerization, solvents may or may not be present. Presence of a solvent is preferred from the viewpoint of controlled reaction and convenience in operation. Examples of solvents include, but are not limited to, water, alcohols, dimethylformamide, and benzene. Examples of chain transfer agents include mercaptoalkylamines, mercaptoalkanols, omega-mercaptocarboxylic acids, alkylene glycols etc. Of these, 2-mercaptoethylamine, 2-mercaptoethanol, and beta-mercaptopropionic acid are preferred. Radical polymerization initiators include azobisisobutyronitrile, benzoyl peroxide, and ammonium persulfate. Of these, azobisisobutyronitrile and benzoyl peroxide are preferred.

The reaction of a vinyl monomer and one or more polymers or copolymers each having an amino, hydroxyl, or carboxyl group (for example, polymers or copolymers of an alkylacrylamide derivative or an alkylmethacrylamide derivative) in the terminal may be easily performed through a conventional acid amide reaction, etherification, or esterification. Preferred vinyl monomers include chloromethylstyrene and propylene methacrylate dioxide.

For example, a random copolymer composed of an alkylacrylamide derivative or an alkylmethacrylamide derivative having a hydroxyl group in the terminal and acrylamide or methacrylamide may be reacted at a temperature between 0 and 100° C. with chlorostyrene in a solvent such as dimethylformamide in the presence of an aqueous 50% KOH aqueous solution and, if necessary, a phase transfer catalyst.

When the thus-prepared macromonomer which corresponds to the structural unit of formula (2), (3), or (4) is polymerized, or copolymerized with vinyl compounds corresponding to formula (1) which are able to radical-polymerize, the aforementioned graft copolymer is obtained.

Examples of the vinyl compounds include styrene, halomethyrstyrene, methyl acrylate, methyl methacrylate, isobutyl cyanoacrylate, acrylonitrile, acrylamide, and vinyl acetate. Of which styrene, halomethylstyrene, methyl acrylate, and methyl methacrylate are preferred.

Of the above-described graft copolymers, those of formula (2b), (2c), (2d), (3a), (3b), (4a), or (4b), which have an acid amide group, a carboxyl group, or a primary amino group in the graft chain, may also be prepared by polymerizing a macromonomer having a structural unit of formula (2a), (3c), and/or (4c), or copolymerizing each of them with a aforementioned vinyl compounds, and subsequently hydrolyzing the resultant product to a suitable extent by a known method.

By varying the degree of polymerization, it is possible to obtain amphipathic graft copolymers which are soluble in water, alcohol, chloroform, dimethylsulfoxide, etc.

Particles composed of these graft copolymers are obtained through dispersion polymerization of a hydrophobic monomer and a hydrophilic macromonomer which corresponds to the structural unit of formula (2), (3), or (4) and through subsequent hydrolysis, which may be performed if necessary. Each of the resultant particles has a form in which the hydrophilic macromonomer is localized in the outer of the particles and the inner of the particles is constituted by the hydrophobic polymer.

Since the surface of the thus-prepared particles are hydrophilic, hydrophilic drugs can be effectively incorporated in the particles. On the other hand, there is the hydrophobic interaction between the hydrophobic drugs and the inner layer composed of a hydrophobic polymer. Hydrophobic drugs may also incorporated to the outer of particles, making use of the amphipathic property of the outer. In other words, since the particles of the present invention are considered to have ability to incorporate drugs effectively without particular dependence on properties of the drugs, the particles of the invention are useful as particulate carriers.

In the present invention, a preferred carrier for drugs is a composition containing a mixture of a graft copolymer (A) (may be referred to as component (a)) and one or more members selected from the group consisting of graft copolymers (B-1) and graft copolymers (B-2) (may be referred to as component (b)). (Hereafter, the composition composed of a component (A) and a component (B) may be referred to as a graft copolymer composition.) Because this graft copolymer composition has two or more kinds of graft chains derived from a hydrophilic macromonomer, it is considered that drugs are effectively incorporated with nanoparticles and are protected against the enzyme in the gastrointestinal tract, and that absorption of drugs by the intestinal tract is enhanced.

The ratio of amounts of components (a) to (b) contained in the drug carrier of the invention is preferably from 1,000:1 to 1:1,000, and particularly preferably from 100:1 to 1:100.

In order to use the above-described graft copolymers as particulate carriers, the graft copolymers are prepared to have the form of microcapsules, microspheres, or nanoparticles.

Microcapsules and microspheres may be obtained by use of conventional methods. Nanoparticles can be obtained by use of a macromonomer method developed by Akashi et al. (Die Angewandte, Macromolekylare Chemie, 132, 81 (1985); Polymer Journal, 24, 959 (1992); Chemical Engineering, page 505, 1994) and dispersion polymerization, to thereby obtain nanoparticles in which a hydrophilic macromonomer is localized in the outer of each particle and the inner of each particle is formed of a hydrophobic polymer.

The particle diameter of nanoparticles varies in accordance with the molecular weight of the macromonomer, reaction conditions under which the macromonomer is prepared, and other factors. When suitable settings and conditions are selected, it is possible to obtain microspheres whose diameter is on the order of micrometers.

As described above, since the graft copolymers or graft copolymer compositions are useful as drug carriers, when the graft copolymers or graft copolymer compositions are mixed with drugs, pharmaceutical compositions exhibiting excellent peroral absorption enhancement effect can be obtained. It is considered that in a drug composition prepared by mixing a graft copolymer or graft copolymer composition with a drug, the graft copolymer or graft copolymer composition and the drug together form a complex. The driving power for the formation of a complex is considered to be electrostatic interaction, hydrogen bonding (i.e., interaction with hydrophilic functional groups on the outer of nanoparticle), hydrophobic interaction (attraction to the inner of the particle).

Drugs which are useful in the preparation of the pharmaceutical composition of the present invention are not particularly limited, and may be hydrophilic or hydrophobic There are the drugs that are expected to be controlled the release or to be enhanced the absorption.

Drugs that are expected to be controlled the release include 1) drugs having a short half-life in blood and 2) drugs having a narrow optimum therapeutic range. Drugs that are expected to be enhanced the absorption, or in other words poor absorptive drugs, include 3) drugs having a low membrane permeability due to their high water-solubility, 4) drugs whose efficacy is hindered from being exerted due to degradation in the gastrointesinal tracts, low absorptive characteristics via the gastrointesinal tracts, etc. and 5) vaccines.

1) Examples of drugs having a short half-life in blood include isosorbide, papaverine, nitroglycerin, ketoprofen, diltiazem, propranolol, isoproterenol, isotipenzyl, aspirin, pindrol, nifedipine, acetazolamide, cephalexin, cefaclor, quinidine, and procain amide.

2) Examples of drugs having a narrow optimum therapeutic range include pilocarpine, theophylline, scopolamine, methyl scopolamine, chlorpheniramine, phenylephrine, trihexyphenidyl, carbetapentane, perphenazine, noscapine, thioridazine, dimethindene, pyridostigmine, and triprolidine.

3) Examples of drugs having a low membrane permeability due to their high water-solubility include phenolsulfonphthalein, salicylic acid and its derivatives, barbituric acid and its derivatives, quaternary ammonium salts such as tubocurarine and suxamethonium, sulfa agents such as sulfanyl acid, sulfanyl acetamide, and sulfaguanidine, quinine, ephedrin, tolazoline, procainamide, atenolol, and chlorothiazide.

4) Examples of drugs whose efficacy is hindered from being exerted due to degradation in the gastrointestinal tracts, low absorptive characteristics via the gastrointestinal tracts include peptides; more specifically, interferon, interleukin, erythropoietin, insulin, neocarcinostatin, parathormone, opioid peptides and calcitonin.

5) Examples of vaccines include those which are considered useful when administered by the oral route. Specific examples of the vaccines include influenza HA vaccine, hepatitis B vaccine, and polio vaccine.

Examples of antigens for the preparation of vaccines include a variety of proteins from: viruses such as influenza A virus, influenza B virus, influenza C virus, rotavirus, cytomegalovirus, RS virus, adenovirus, AIDS virus (HIV), hepatatis A virus, hepatitis B virus, hepatitis C virus, varicella-zoster virus, herpes simplex virus (type 1 and type 2), adult T cell leukemia virus (ATLV), coxsackie virus, enterovirus, exanthema subtium virus, measles virus, rubella virus, mumps virus, polio virus, Japanese encephalitis virus, and rabies virus; bacteria such as Streptococcus caries, Vibrio cholerae, *Haemophilus influenzae, Streptococcus pneumoniae, Bordetella pertussis, Corynebacterium diphtheriae,* and *Clostridium tetani*; rickettsias such as chlamydia; and protozoas such as malaria plasmodium. Moreover, the above-listed viruses, bacteria, rickettsias, and protozoas by themselves may be used as antigens after their phathogenity has been weakened. Among the above-listed drugs, those that are expected to be enhanced absorption (i.e., poor absorptive drugs) are preferably used in the present invention. Peptides are more preferred, and opioid peptide and calcitonin are particularly preferred.

It is considered that, when the above-described complexes are administered perorally, most drugs are delivered to the vicinity of the microvilli of the gastrointestinal tract while retaining their complex forms, since the particles of the complexes are very small (J. Kreuter et al., International Journal of Pharmaceutics, 55, 39 (1989)). Moreover, since the graft copolymers used in the present invention have hydrophilic groups on the outer of them, the compatibility of the complexes with the membranes of the gastrointestinal tract is high.

In short, it is considered that a particulate carrier composed of the graft copolymer or graft copolymer composition of the present invention, particularly a complex of nanoparticle and drug, can accumulate the drug at a high concentration in the vicinity of the membranes. As a result, absorption of poor absorptive drugs can be improved.

Moreover, peptides and similar drugs which are easily degraded by digestive enzymes in the gastrointestinal tract can be protected from attacks by the enzymes when formulated to have the form of particles.

In addition, the complexes of particles and drugs, having the compatibility with the membranes, are considered to decrease the transit time of drugs in the gastrointestinal tract. Consequently, controlled release of the drugs is expected, as the drugs retain the absorption site, i.e., in the gastrointestinal tract, over prolonged periods.

In pharmaceutical compositions of the present invention, the ratio of the amount of the graft copolymer or graft copolymer composition to the amount of the drug is adjusted in accordance with the drug to be employed.

In practice, a mixture or a complex of the graft copolymer or graft copolymer composition and a drug are formulated into a drug preparation by known method and administered perorally. Alternatively, the mixture or the complex of the graft copolymer or graft copolymer composition and a drug may be encapsulated in soft capsules.

The physical form of the drug preparation is not particularly limited. The drugs preparation may take the solid formulation such as tablets, granules, powders, and capsules etc; or the liquid formulation such as syrups, elixirs, suspensions, emulsions etc. When these drug preparations are manufactured, it goes without saying that customary additives such as excipients, binders, lubricants, and disintegrants may also be mixed.

The drug absorption enhancement effect of the pharmaceutical compositions of the present invention is not reduced even under conditions of low pH such as at a pH of 1.2. Moreover, this effect is not reduced at the body temperature of 40° C. Therefore, the pharmaceutical composition of the present invention are particularly useful for peroral administrations.

As will be described in the Example section hereinbelow, the drug absorption enhancement effect of the pharmaceutical compositions of the present invention is greatly improved when the compositions are administered in a divided manner with intervals of a certain period. Accordingly, by suitably designing the manner of dosage or means of formulation of the drug preparations (for example, by administering a single dose in two or more divided portions, or by incorporating a rapid release formulation and a slow release formulation in combination within a single drug preparation), the drug absorption enhancement effect of the pharmaceutical compositions of the present invention is even further improved.

EXAMPLES

The present invention will next be described by way of reference examples, working examples, and test examples, which should not be construed as limiting the invention.

Reference Example 1

Graft copolymer having poly N-isopropylacrylamide as the graft chain (Graft copolymer (A-1)):

1-1. Synthesis of an N-isopropylacrylamide oligomer

N-isopropylacrylamide (20 g, Kojin), 2,2'-azobisisobutyronitrile (AIBN) (0.6 g), and 2-mercaptoethanol (0.20 g) were dissolved in ethanol (80 ml). The solution was polymerized for 7 hours at 60° C. in an atmosphere of nitrogen. When polymerization was completed, the solvent contained in a reaction mixture was removed by use of an evaporator. The prepolymer was re-dissolved in distilled water, heated, and centrifugally separated at a temperature of 60° C. or higher for purification, and the resultant purified product was freeze-dried. The yield of the polymer was 83%. The number average molecular weight (Mn) of the polymer determined by gel permeation chromatography (GPC) was 3,400.

1-2. Synthesis of an N-isopropylacrylamide macromonomer

The N-isopropylacrylamide oligomer (8 g) obtained in Step 1-1 was dissolved in dimethylformamide (DMF) (50 ml). To the solution was added 50% KOH (3.3 g), and the resultant mixture was stirred for 30 minutes at 30° C. Tetrabutylphosphate bromide (500 mg) was added, and subsequently, chloromethylstyrene (4.65 g) was added. The mixture was allowed to react for 72 hours at 30° C. The precipitation were removed by filtration, and the reaction mixture was dialyzed and freeze-dried. The yield of the macromonomer was 82%. The number average molecular weight (Mn) of the macromonomer determined by GPC was 3,500. The macromonomer was soluble in water and in ethanol.

Figure 1B:
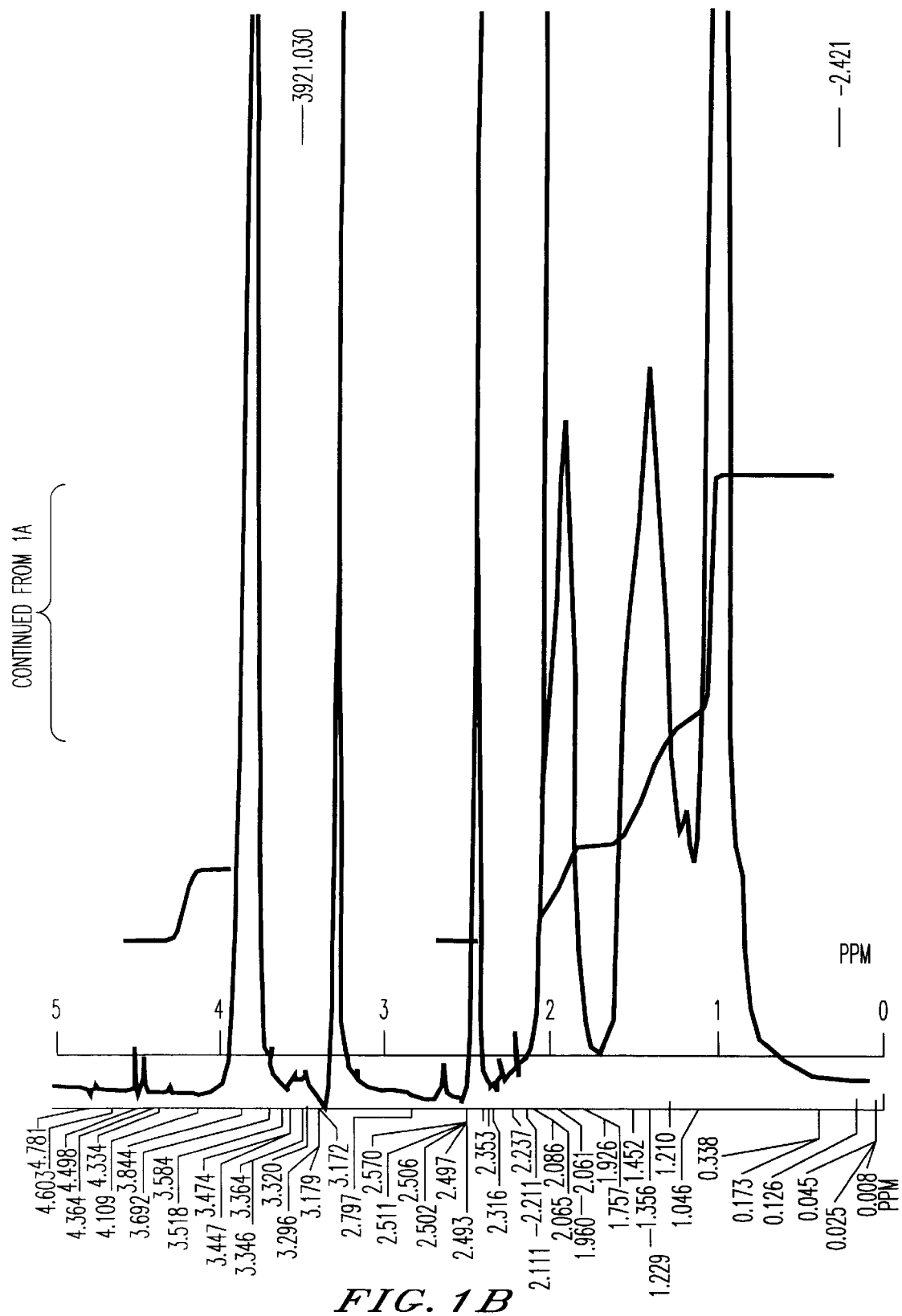

FIG. 1 is the proton NMR chart obtained for the thus-obtained N-isopropylacrylamide macromonomer in DMSO-$D^6$.

The chart shows peaks attributed to the vinyl protons of styrene ($\delta$=5.3–6.0 ppm and 6.6–7.0 ppm) and a peak attributed to the proton of the benzene nucleus in the vicinity of 7.5 ppm.

1-3. Copolymerization of an N-isopropylacrylamide macromonomer and styrene (Synthesis of a graft copolymer (A-1)); and preparation of nanoparticles The macromonomer obtained in Step 1-2 (Mn=3,500) (635 mg), styrene (520 mg), and AIBN (8.5 mg) were dissolved in ethanol (5 ml). The solution was allowed to react for 24 hours at 60° C. After polymerization, the unreacted substance and the solvent were removed by dialysis, and the polymer was freeze-dried. The polymer was soluble in chloroform and in DMSO. The particle diameter of the graft copolymer was 430 nm, as measured by the dynamic light scattering spectrophotometry.

Figure 2:
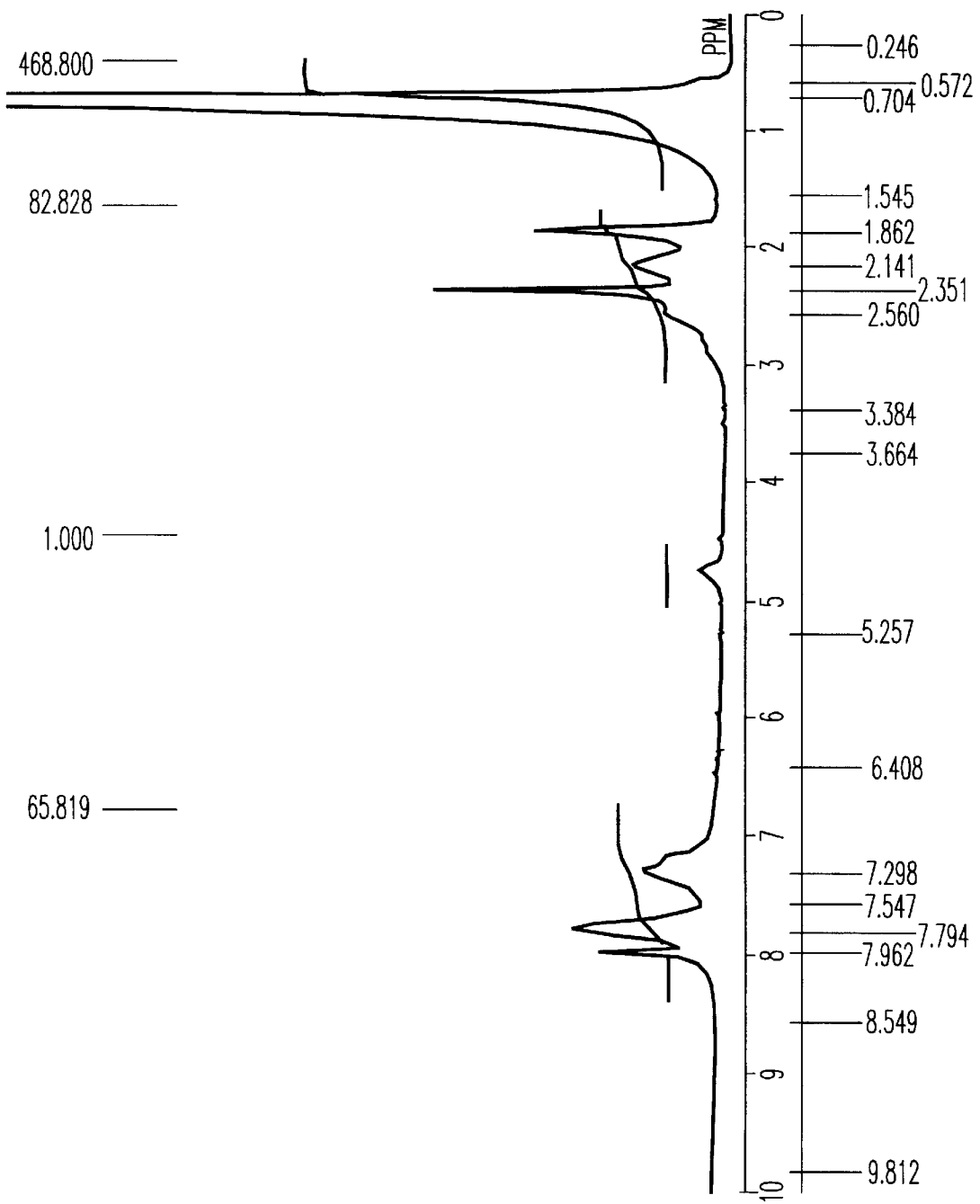
FIG. 2 is a proton NMR chart of the graft copolymer synthesized in Reference Example 1-3, in which the hydrophobic backbone was consisted of polystyrene and the hydrophilic branches were consisted of poly N-isopropylacrylamide.

FIG. 2 is the proton NMR chart obtained for the graft copolymer in DMSO-$D^6$.

In the chart, the vinyl protons of styrene ($\delta$=5.3–6.0 ppm and 6.6–7.0 ppm) observed in the aforementioned macromonomer disappeared, and in their place were observed peaks attributed to the protons of the methylene group of styrene ($\delta$=1.8–2.6 ppm) and a peak attributed to the proton of the benzene nucleus in the vicinity of 7.5 ppm.

Reference Example 2

Graft copolymer which has a random copolymer composed of N-isopropylacrylamide and acrylamide as the graft chain (the proportion of N-isopropylacrylamide contained in the graft chain being 53%) (Graft copolymer (A-2))

2-1. Synthesis of an oligomer of a random copolymer composed of N-isopropylacrylamide and acrylamide An N-isopropylacrylamide monomer (8.70 g, 75 mmol) and an acrylamide monomer (1.44 g, 25 mmol) were dissolved in ethanol (50 ml). 2-Mercaptoethanol (0.273 g, 3.50 mmol) as a chain transfer agent and azobisisobutyronitrile (0.164 g, 1.00 mmol) as a radical polymerization initiator were added. Polymerization was performed for 6 hours at 60° C. in an atmosphere of nitrogen, to thereby synthesize the title oligomer. After reaction, the solvent was evaporated and the residue, after being dissolved in acetone, was allowed to precipitate in hexane to thereby recover the product. The reprecipitation was conducted several times so as to purify the oligomer. The molecular weight (Mn) of the oligomer was 3,100, as determined by GPC.

Figure 3:
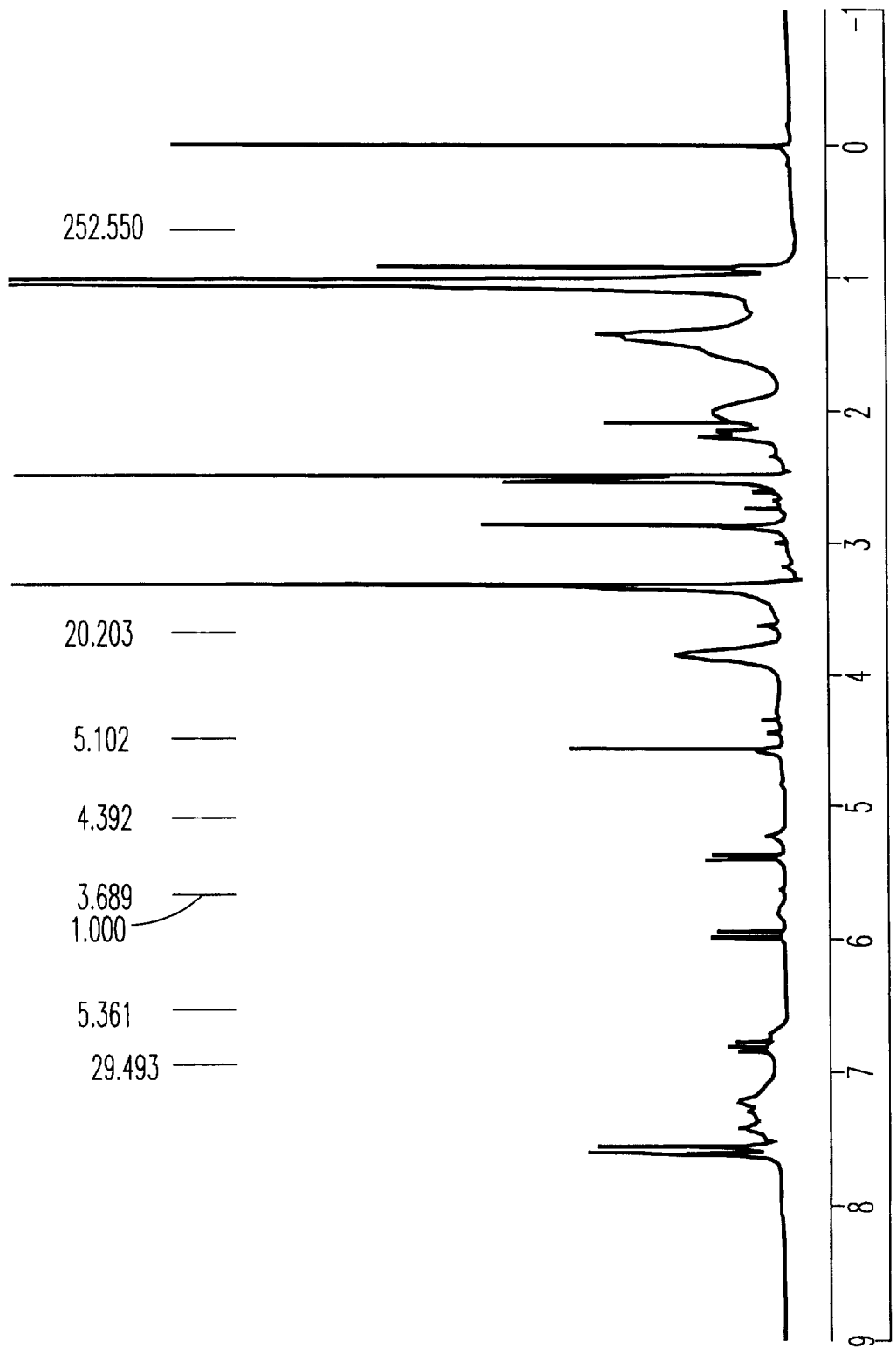
FIG. 3 is a proton NMR chart of the macromonomer that was synthesized in Reference Example 2-2, which was consisted of random-copolymer of N-isopropylacrylamide and acrylamide.

2-2. Synthesis of a macromonomer of a random copolymer composed of N-isopropylacrylamide and acrylamide The oligomer (4 g, 1.29 mmol) obtained in 2-1 was dissolved in dimethylformamide (50 ml). To the solution were added sodium hydride (0.062 g, 2.58 mmol) and tetrabutylphosphonium bromide (2.189 g, 6.45 mmol) as a phase transfer catalyst, and the mixture was stirred for 60 minutes. Thereafter, p-chloromethylstyrene (4.10 g, 26.7 mmol) was added, and the mixture was stirred for 48 hours at 30° C. After being stirred, the solvent was evaporated and the residue, after being dissolved in acetone, was allowed to precipitate in hexane to thereby recover the product. The reprecipitation was conducted several times for purification. The introduction rate of vinyl benzyl group was calculated based on the $^1$H-NMR data. As a result, it was confirmed that vinyl benzyl group had been almost quantitatively introduced (FIG. 3). The molecular weight (Mn) of the obtained macromonomer was determined to be 4,600 by GPC.

2-3. Copolymerization of styrene and a macromonomer of a random copolymer composed of N-isopropylacrylamide and acrylamide (Synthesis of a graft copolymer (A-2); and preparation of nanoparticles)

The macromonomer obtained in Step 2-2 (0.300 g, 0.065 mmol) and styrene (0.500 g, 4.80 mmol) were dissolved in ethanol (5 ml). Azobisisobutyronitrile (0.008 g, 0.049 mmol) as a radical polymerization initiator was added, and polymerization was performed in a deaerated sealed tube for 48 hours at 60° C. After reaction, the contents of the tube were subjected to several repetitions of centrifugal separation and redispersal in ethanol. In the last step, the graft copolymer was dispersed in water to thereby conclude purification. Measurement by the dynamic light scattering spectrophotometry revealed that the average particle size was 494 nm.

Reference Example 3

Graft copolymer which has a random copolymer composed of N-isopropylacrylamide and acrylic acid as the graft chain (the proportion of N-isopropylacrylamide contained in the graft chain being 53%) (Graft copolymer (A-3))

The nanoparticles obtained in Step 2-3 were dispersed in 2N-HCl, and then hydrolyzed for 12 hours at 95° C., to thereby substitute the acrylamide group of the macromonomer into acrylic acid group. After reaction, dialysis was performed for purification. The acrylamide present in the outer of the nanoparticles was confirmed by IR to have been hydrolyzed. Thus, the title graft copolymer was obtained. The average particle size was found to be 311 nm by the dynamic light scattering spectrophotometry.

Reference Example 4

Graft copolymer which has a random copolymer composed of N-isopropylacrylamide and acrylamide as the graft chain (the proportion of N-isopropylacrylamide contained in the graft chain being 25%) (Graft copolymer (A-4))

4-1. Synthesis of an oligomer of a random copolymer composed of N-isopropylacrylamide and acrylamide An N-isopropylacrylamide monomer (3.48 g, 30 mmol) and an acrylamide monomer (4.03 g, 70 mmol) were dissolved in a solvent mixture (50 ml) of ethanol and water (1:1 (v/v)). 2-Mercaptoethanol (0.273 g, 3.50 mmol) as a chain transfer agent and azobisisobutyronitrile (0.164 g, 1.00 mmol) as a radical polymerization initiator were added. Polymerization was performed for 6 hours at 60° C. in an atmosphere of nitrogen, to thereby synthesize the title oligomer. After reaction, the solvent was evaporated and the residue, after being dissolved in acetone, was allowed to precipitate in hexane to thereby recover the product. The reprecipitation was conducted several times so as to purify the oligomer. The molecular weight (Mn) of the obtained oligomer was determined to be 2,100 by GPC.

Figure 4:
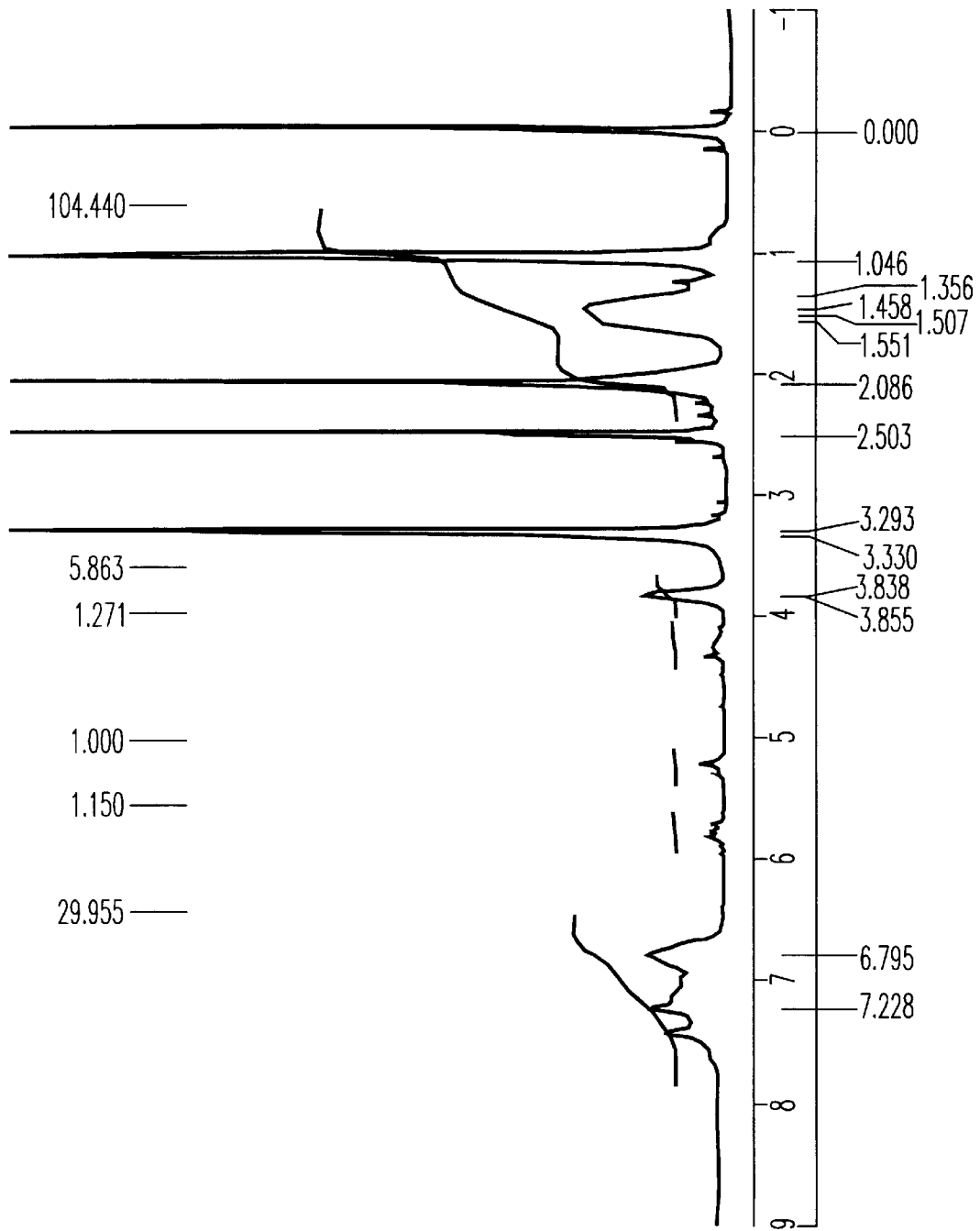
FIG. 4 is a proton NMR chart of the macromonomer that was synthesized in Reference Example 4-2, which was consisted of random-coplymer of N-isopropylacrylamide and acrylamide.

4-2. Synthesis of a macromonomer of a random copolymer composed of N-isopropylacrylamide and acrylamide The oligomer (3.5g, 1.66 mmol) obtained in Step 4-1 was dissolved in dimethylformamide (50 ml). To the solution were added sodium hydride (0.080 g, 3.32 mmol) and tetrabutylphosphonium bromide (2.82 g, 8.30 mmol) as a phase transfer catalyst, and the mixture was stirred for 60 minutes. Thereafter, p-chloromethylstyrene (3.58 g, 23.3 mmol) was added, and the mixture was stirred for 48 hours at 30° C. After reaction, the solvent was evaporated and the residue, after being dissolved in acetone, was allowed to precipitate in hexane to thereby recover the product. The reprecipitation was conducted several times for purification. The introduction rate of vinyl benzyl group was calculated based on the $^1$H-NMR data. As a result, it was confirmed that vinyl benzyl group had been introduced almost quantitatively (FIG. 4). The molecular weight (Mn) of the obtained macromonomer was determined to be 2,100 by GPC.

4-3. Copolymerization of styrene and a macromonomer of a random copolymer composed of N-isopropylacrylamide and acrylamide (Synthesis of a graft copolymer (A-4); and preparation of nanoparticles)

The macromonomer obtained in Step 4-2 (0.300 g, 0.065 mmol) and styrene (0.550 mg, 5.28 mmol) were dissolved in a solvent mixture (5 ml) of ethanol and water (1:1 (v/v)). Azobisisobutyronitrile (0.0089 g, 0.0542 mmol) as a radical polymerization initiator was added, and copolymerization was performed in a deaerated sealed tube for 48 hours at 60° C. After reaction, the contents of the tube were subjected to several repetitions of centrifugal separation and redispersal in ethanol. In the last step, the graft copolymer product was dispersed in water to thereby conclude purification. Measurement by the dynamic light scattering spectrophotometry revealed that the average particle size was 347 nm.

Reference Example 5

Graft copolymer which has a random copolymer composed of N-isopropylacrylamide and acrylic acid as the graft chain (the proportion of N-isopropylacrylamide contained in the graft rain being 25%) (Graft copolymer (A-5))

The nanoparticles obtained in Step 4-3 were dispersed in 2N-HCl, and then hydrolyzed for 12 hours at 95° C., to thereby substitute the acrylamide group of the macromonomer into acrylic acid group. After reaction, dialysis was performed for purification. The acrylamide present in the outer of the nanoparticles was confirmed by IR to have been hydrolyzed. Thus, the title graft copolymer was obtained. The average particle size determined by the dynamic light scattering spectrophotometry was 482 nm.

Reference Example 6

Graft copolymer which has a random copolymer composed of N-isopropylacrylamide and acrylamide as the graft chain (the proportion of N-isopropylacrylamide contained in the graft chain being 68%) (Graft copolymer (A-6))

6-1. Synthesis of an oligomer of a random copolymer composed of N-isopropylacrylamide and acrylamide An N-isopropylacrylamide monomer (12.75 g, 112.7 mmol) and an acrylamide monomer (1.82 g, 16.1 mmol) were dissolved in ethanol (50 ml). 2-Mercaptoethanol (0.351 g, 4.50 mmol) as a chain transfer agent and azobisisobutyronitrile (0.211 g, 1.29 mmol) as a radical polymerization initiator were added. Polymerization was performed for 6 hours at 60° C. in an atmosphere of nitrogen, to thereby synthesize the title oligomer. After reaction, the solvent was evaporated and the residue, after being dissolved in acetone, was allowed to precipitate in hexane to thereby recover the product. The reprecipitation was conducted several times so as to purify the oligomer. The molecular weight (Mn) of the obtained oligomer was 4,400, as determined by GPC.

Figure 5:
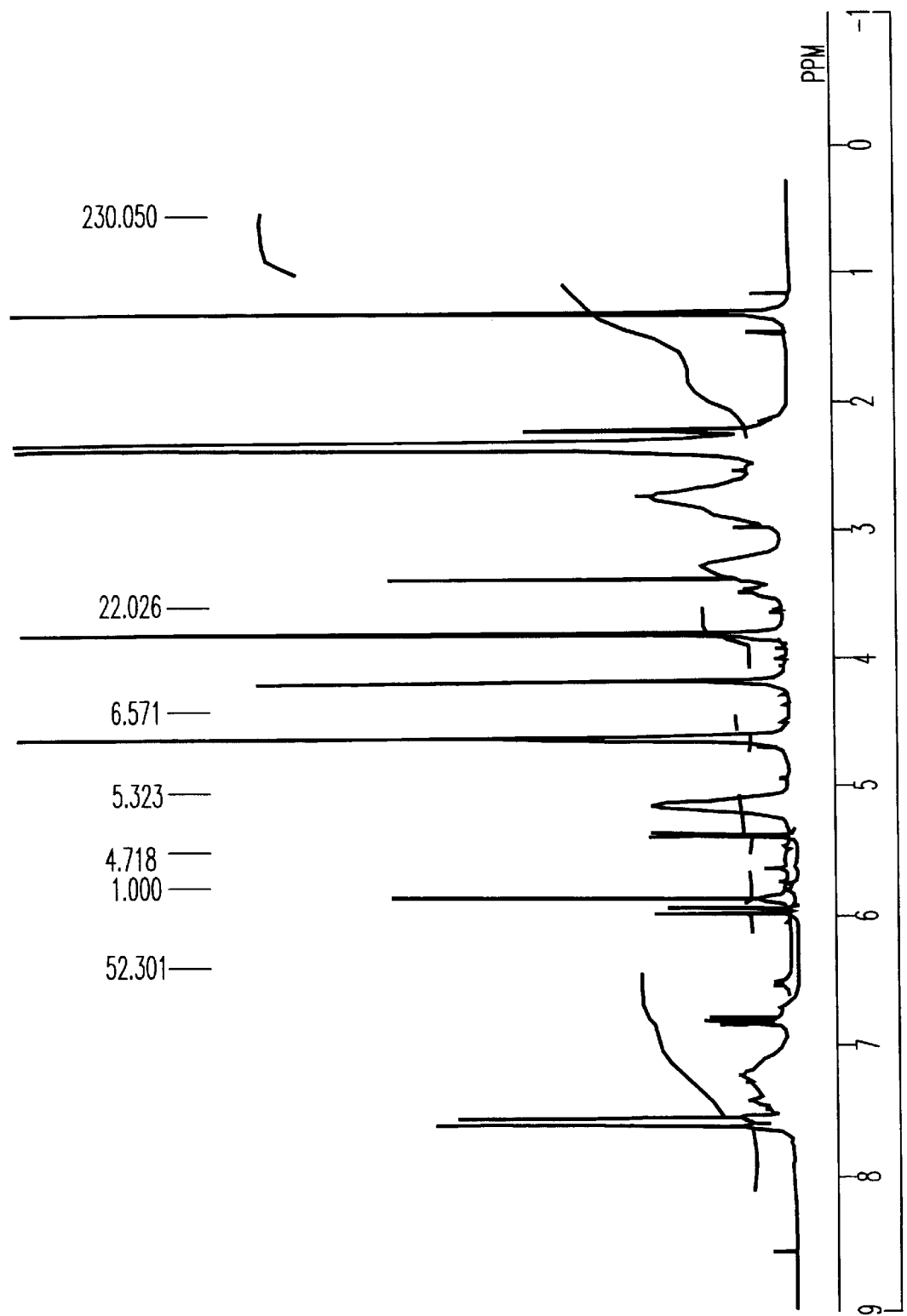
FIG. 5 is a proton NMR chart of the macromonomer that was synthesized in Reference Example 6-2, which was consisted of random-copolymer of N-isopropylacrylamide and acrylamide.

6-2. Synthesis of a macromonomer of a random copolymer composed of N-isopropylacrylamide and acrylamide The oligomer (3 g, 0.66 mmol) obtained in Step 6-1 was dissolved in dimethylformamide (50 ml). To the solution were added sodium hydride (0.032 g, 1.32 mmol) and tetrabutylphosphonium bromide (1.12 g, 3.30 mmol) as a phase transfer catalyst, and the mixture was stirred for 60 minutes. Thereafter, p-chloromethylstyrene (2.97 g, 19.3 mmol) was added, and the mixture was stirred for 48 hours at 30° C. After reaction, the solvent was evaporated and the residue, after being dissolved in acetone, was allowed to precipitate in hexane to thereby recover the product. The reprecipitation was conducted several times for purification. The introduction rate of vinyl benzyl group was calculated based on the $^1$H-NMR data. As a result, it was confirmed that vinyl benzyl group had been introduced almost quantitatively (FIG. 5). The molecular weight (Mn) of the obtained macromonomer was determined to be 7,200 by GPC.

6-3. Copolymerization of styrene and a macromonomer of a random copolymer composed of N-isopropylacrylamide and acrylamide (Graft copolymer (A-6); and preparation of nanoparticles)

The macromonomer obtained in Step 6-2 (0.374 g, 0.052 mmol) and styrene (0.650 mg, 6.25 mmol) were dissolved in ethanol (5 ml). Azobisisobutyronitrile (0.010 g, 0.063 mmol) as a radical polymerization initiator was added, and copolymerization was performed in a deaerated sealed tube for 48 hours at 60° C. After reaction, the contents of the tube were subjected to several repetitions of centrifugal separation and redispersal in ethanol. In the last step, the graft copolymer product was dispersed in water to thereby conclude purification. Measurement by the dynamic light scattering spectrophotometry revealed that the average particle size was 253 nm.

Reference Example 7

Graft copolymer which has a random copolymer composed of N-isopropylacrylamide and acrylic acid as the graft chain (the proportion of N-isopropylacrylamide contained in the graft chain being 68%) (Graft copolymer (A-7))

The nanoparticles obtained in Step 6-3 were dispersed in 2N-HCl, and then hydrolyzed for 12 hours at 95° C., to thereby substitute the acrylamide group of the macromonomer chain into acrylic acid group. After reaction, dialysis was performed for purification. The acrylamide present in the outer of the nanoparticles was confirmed by IR to have been hydrolyzed. Thus, the title graft copolymer was obtained. The average particle size determined by the dynamic light scattering spectrophotometry was 769 nm.

The structure of the graft copolymers synthesized in Reference Examples 3, 5, and 7 is shown below.

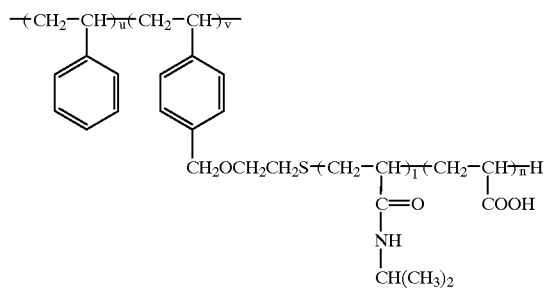

Reference Example 8

Preparation of a graft copolymer having poly-tert-butylmethacrylate as the graft chain (Graft copolymer (B-1-1)):

8-1. Synthesis of a tert-butylmethacrylate (t-BMA) oligomer

A tert-butylmethacrylate monomer (25.02 g, 175.8 mmol) was dissolved in tetrahydrofuran (THF) (50 ml). 2-Mercaptoethanol (0.345 g, 4.42 mmol) as a chain transfer agent and azobisisobutyronitrile (AIBN) (0.288 g, 1.76 mmol) as a radical polymerization initiator were added. Polymerization was performed for 6 hours at 60° C. in an atmosphere of nitrogen, to thereby synthesize a t-BMA oligomer. After reaction, the reaction substance was purified by a series of reprecipitation through use of a mixture of methanol and water (1:1). The molecular weight (Mn) of the obtained polymer was determined to be 3,620 by GPC.

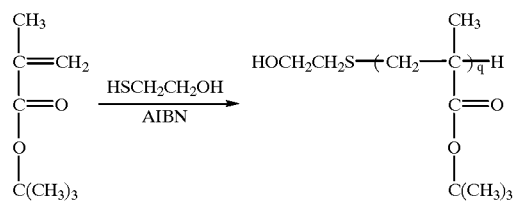

8-2. Synthesis of a tert-BMA macromonomer

The t-BMA oligomer (5.00 g, 1.38 mmol) obtained in Step 8-1 was dissolved in dimethylformamide (DMF) (50 ml). To the solution was added aqueous 50% KOH (0.774 g) and, as a phase transfer catalyst, tetrabutylphosphonium bromide (TBPB) (0.468 g, 1.38 mmol). The resultant mixture was stirred for 24 hours at 30° C. Subsequently, chloromethylstyrene (4.24 g, 27.6 mmol) was added. The mixture was allowed to react for 48 hours at 30° C. After reaction, the reaction substance was subjected to a purification step, in which reprecipitation was performed through use of a 1:1 water-methanol mixture. The introduction rate of vinyl benzyl group was calculated based on the $^1$H-NMR data. As a result, it was confirmed that vinyl benzyl group had been introduced almost quantitatively. The molecular weight (Mn) of the obtained macromonomer was determined to be 4,070 by GPC.

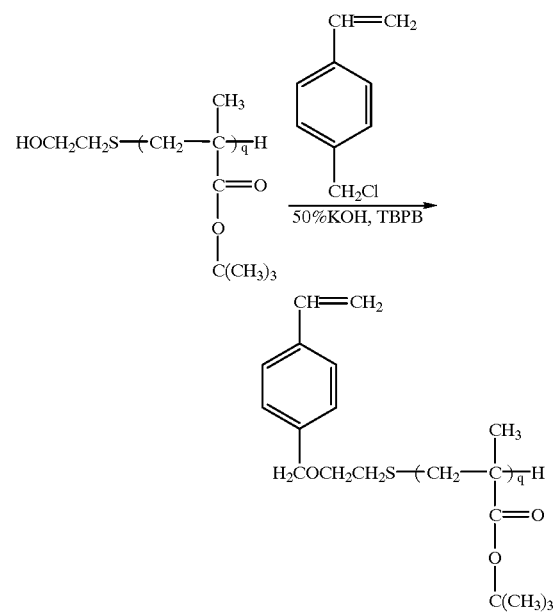

8-3. Copolymerization of the t-BMA macromonomer and styrene (Synthesis of a graft copolymer (B-1-1) and preparation of nanoparticles)

The t-BMA macromonomer obtained in Step 8-2 (0.300 g, 0.083 mmol) and styrene (0.345 g, 3.32 mmol) were dissolved in ethanol (5 ml). AIBN, a radical polymerization initiator, was added (5.88 mg, 0.036 mmol) thereto, and copolymerization was performed in a deaerated sealed tube for 48 hours at 60° C. After reaction, the contents of the tube were purified by dialysis. Measurement by the dynamic light scattering spectrophotometry revealed that the average particle size was 679 nm.

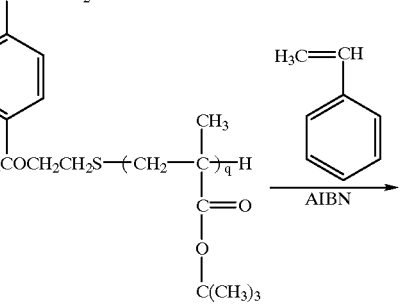

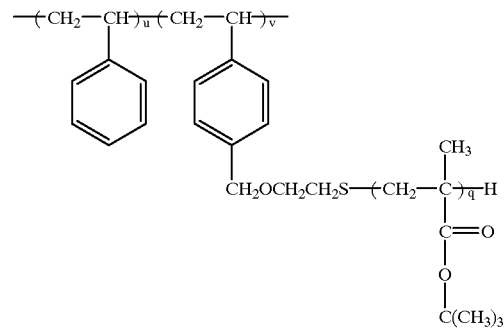

Reference Example 9

A-graft copolymer having polymethacrylic acid as the graft chain (Graft copolymer (B-1-2)):

The nanoparticles obtained in Step 8-3 were dispersed in 2N-HCl—ethanol, and hydrolyzed for 12 hours at 80° C., to thereby convert the ester of the macromonomer into carboxyl group. After reaction, the nanoparticles were purified through dialysis. Measurement by the dynamic light scattering spectrophotometry revealed that the average particle size of the nanoparticles was 835 nm.

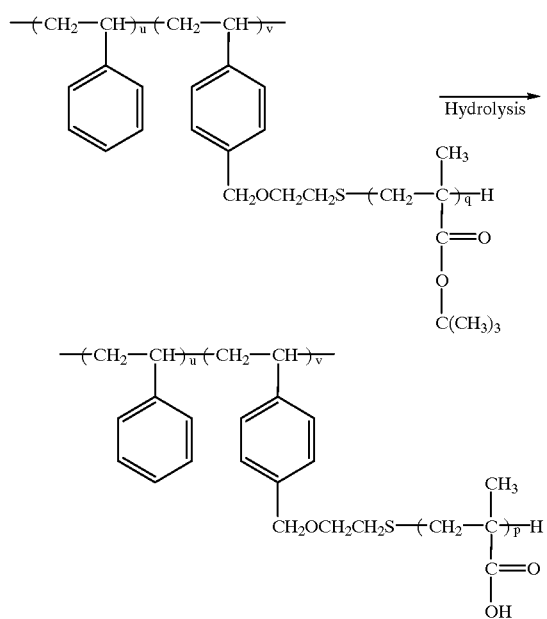

Reference Example 10

A graft copolymer having poly N-vinylacetamide as the graft chain (Graft copolymer (B-2-1)):

10-1. Synthesis of an N-vinylacetamide oligomer

An N-vinylacetamide (NVA) monomer (10 g, 117.6 mmol) was dissolved in ethanol (50 ml). 2-Mercaptoethanol (2.3 g, 29.44 mmol) as a chain transfer agent and azobisisobutyronitrile (0.197 g, 1.2 mmol) as a radical polymerization initiator were added thereto, and polymerization was performed for 6 hours at 60° C. in an atmosphere of nitrogen, to thereby synthesize an NVA oligomer. After reaction, the reaction substance was subjected to reprecipitation several times through use of diethylether for purification. The molecular weight (Mn) of the obtained oligomer was determined to be 2,500 by GPC.

10-2. Synthesis of an NVA macromonomer

The NVA oligomer (1.875 g, 0.75 mmol) obtained in Step 10-1 was dissolved in dimethylformamide (50 ml). To the solution was added aqueous 50% KOH (0.84 g, 7.5 mmol) and, as a phase transfer catalyst, tetrabutylphosphonium bromide (0.127 g, 0.374 mmol). The resultant mixture was stirred for 30 minutes, and subsequently, chloromethylstyrene (1.152 g, 7.5 mmol) was added. The mixture was allowed to react for 48 hours at 30° C., to thereby obtain an NVA macromonomer.

After reaction, the reaction substance was subjected to a purification step, in which reprecipitation was performed several times through use of diethylether. The introduction rate of vinyl benzyl group was calculated based on the $^1$H-NMR data. As a result, it was confirmed that vinyl benzyl group had been introduced almost quantitatively. The molecular weight (Mn) of the obtained macromonomer was determined to be 2,600 by GPC.

10-3. Copolymerization of the NVA macromonomer and styrene (Synthesis of a graft copolymer (B-2-1); and preparation of nanoparticles)

The NVA macromonomer obtained in Step 10-2 (0.25 g, 0.096 mmol) and styrene (0.23 ml, 1.99 mmol) were dissolved in ethanol (5 ml). A radical polymerization initiator azobisisobutyronitrile (3.34 mg, 0.02 mmol) was added, and copolymerization was performed in a deaerated sealed tube for 48 hours at 60° C. After reaction, the contents of the tube were dialyzed so as to remove unreacted substances. Measurement by the dynamic light scattering spectrophotometry revealed that the average particle size of the graft copolymer was 257 nm.

Reference Example 11

Graft copolymer having polyvinylamine as the graft chain (Graft copolymer (B-2-2))

The nanoparticles obtained in Step 10-3 were dispersed in 2N-HCl, and hydrolyzed for 12 hours at 100° C., to thereby hydrolyze the amide bond in the macromonomer chain. The nanoparticles, after reaction, were purified through dialysis. Measurement by the dynamic light scattering spectrophotometry revealed that the average particle size of the nanoparticles was 273 nm.

Example 1

Preparation of a complex of nanoparticles and phenolsulfonphthalein (PSP) (a nanoparticle preparation of PSP)

A monosodium salt of PSP (PSP-Na) was dissolved in phosphate buffer (pH 7.0, 0.50 mM) containing sucrose at a concentration of 3.15 w/v %, so that the concentration of the PSP-Na was 20 mg/ml. To the solution was added the freeze-dried product (graft copolymer (A-1)) obtained in Step 1-3 of Reference Example 1 at a concentration of 20 mg/ml. The mixture was brought to a uniform dispersion, to thereby obtain a nanoparticle preparation. Independently, an aqueous PSP-Na solution in which nanoparticles were not dispersed were prepared in a similar manner, and this product was used as a control preparation.

Example 2

In vivo evaluation of the complex of nanoparticles and phenolsulfonphthalein (PSP)

2-1. Method

SD male rats (7 weeks old, about 200 g) were fasted for 24 hours. Under etherization, laparotomy was performed. By use of an injection needle, which was inserted through the pyrolus, the nanoparticle preparation (0.5 ml) prepared in Example 1 or the control preparation (0.5 ml) was administered duodenumally to the rats (dose: 9.4 mg in terms of PSP per rat; n=6). The cut was closed immediately after administration. Blood was collected from the carotid artery at 0.5, 1, 2, 4, 8, 12, and 24 hours following the administration.

In accordance with the method of K. Higaki (Journal of Pharmaceutical Science, 79, 334, 1990), the plasma PSP concentration of each rat was measured. The plasma (0.3 ml) that had been centrifugally separated from the collected blood, purified water (0.3 ml), and aqueous 0.1 N NaOH solution (0.9 ml) were mixed. The mixture was filtered through use of an ultrafilter membrane (molecular weight of fractionation=10,000), to thereby remove proteins, etc. The filtrate was used as a sample solution. Separately, standard solutions were prepared through use of aqueous PSP-Na solutions (starting from 9.4 mg/ml in terms of PSP, a series of 2-fold dilutions) (0.3 ml each), a blank plasma from each rat (0.3 ml), and aqueous 0.1 N NaOH solution (0.9 ml) were mixed and ultrafiltered. For each of the sample solutions and standard solutions, absorption was determined through use of a spectrometer at the wavelength of 560 nm. Based on the results obtained from the standard solutions, a calibration curve was obtained, and the plasma PSP concentrations were measured. Based on the obtained time—plasma PSP concentration profile, pharmacokinetic parameters were calculated.

2-2. Results

Figure 6:
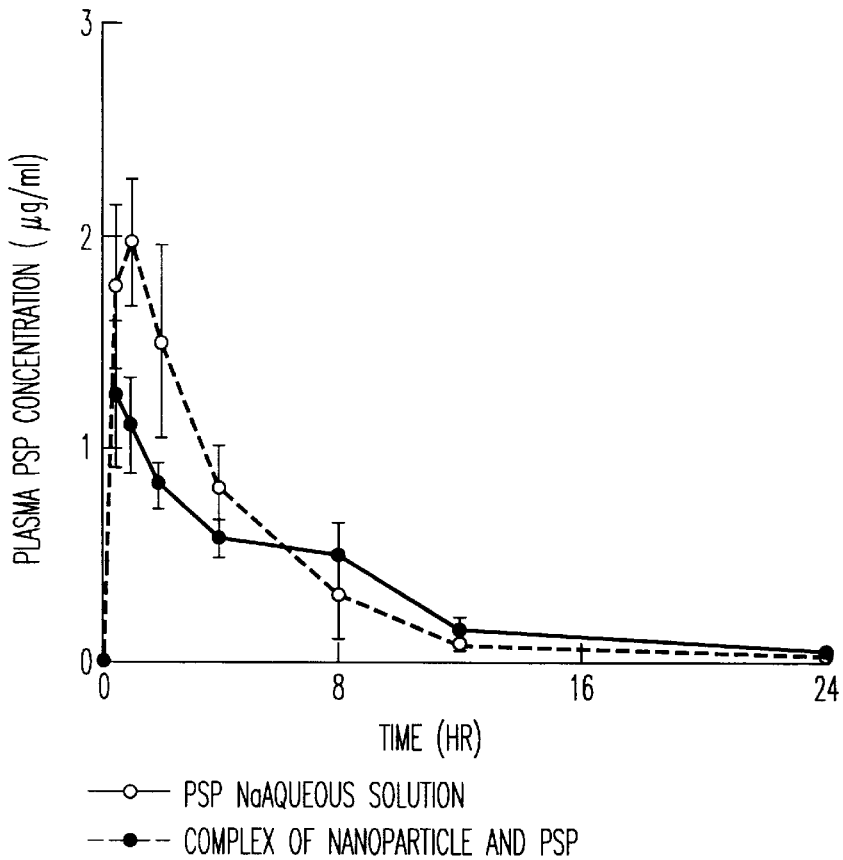
FIG. 6 is a graph showing the plasma phenolsulfonphthalein concentration as a function of time (mean±S.D.), after phenolsulfophthalein was duodenally administered to rats in Example 2.

The time—plasma PSP concentration profile is shown in FIG. 6, and the calculated pharmacokinetic parameters are shown in Table 1. As is apparent from Table 1, the mean residence time (MRT) of PSP was significantly increased when PSP was mixed with nanoparticles (level of significance: 1%). Thus, it was proved that the nanoparticle preparation (i.e, a complex of nanoparticles and PSP) making use of the graft copolymer of the present invention has controlled release properties.

TABLE 1

|  | $AUC_{0-inf}$ | $C_{max}$ | $t_{max}$ | (mean ± S.D.) $MRT_{0-24h}$ |
|---|---|---|---|---|
| Aq. PSP-Na sol. (control prep.) | 9.97 ± 2.20 | 2.00 ± 0.29 | 0.92 ± 0.20 | 4.57 ± 0.34 |
| Complex of PSP & nanoparticles (Example 1) | 9.53 ± 1.15 | 1.28 ± 0.32 | 0.58 ± 0.20 | 6.74 ± 0.38 |

Example 3

Preparation of a complex of nanoparticles and salmon calcitonin (sCT) (a nanoparticle preparation of sCT)

An aqueous sCT solution having a concentration of 200 µg/ml and a dispersion (dispersion medium: water) of the nanoparticles obtained in Step 1-3 of Reference Example 1 (graft copolymer (A-1)), which had a concentration of 60 mg/ml, were independently prepared. The two were mixed in equal amounts and the nanoparticles were dispersed uniformly, to thereby obtain a nanoparticle preparation. Separately, an aqueous sCT solution in which nanoparticles were not dispersed was prepared in a manner similar to that described above, to thereby obtain a control preparation.

Example 4

In vivo evaluation of the complex of nanoparticles and salmon calcitonin (sCT)

4-1. Method

To SD male rats (7 weeks old, about 200 g) fasted for 24 hours were administered perorally the nanoparticle preparation (0.5 ml) prepared in Example 3 or the control preparation (0.5 ml) (n=5). After administration, blood was collected from the tail vein of each rat in an amount of about 60 µl at 40 minutes, 80 minutes, 2, 3, 4, 6, and 8 hours following the administration.

Using a 634 $Ca^{++}$/pH analyzer (Ciba-Coning), the concentration of ionized calcium in the collected blood was measured. The difference between the ionized calcium concentration at time 0 and that at each of the aforementioned times was calculated and plotted. From the plots, presence or absence of the effect of absorption enhancement obtained through formation of nanoparticles was determined.

In this connection, sCT is known to have the pharmacological effect of reducing the blood ionized calcium concentration.

4-2. Results

Figure 7:
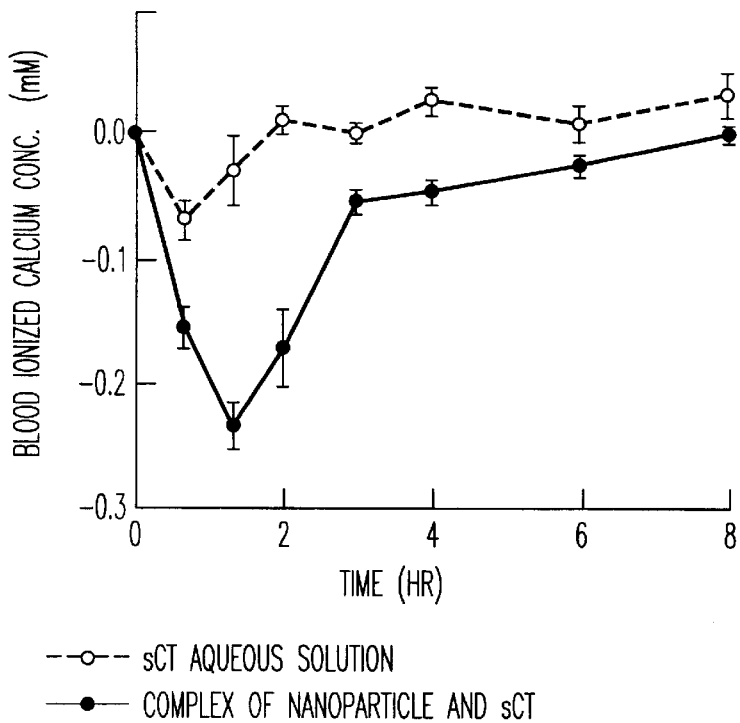
FIG. 7 is a graph showing the change of ionized calcium concentration in blood (mean±S.E.) as a function of time, after salmon calcitonin was perorally administered to rats in Example 4.

The results are shown in FIG. 7. As is apparent from FIG. 7, the blood ionized calcium concentration was slightly decreased when the aqueous sCT solution (i.e., a control preparation) was administered, however this effect of reducing the blood ionized calcium concentration was considerably enhanced when the nanoparticle preparation (a complex of nanoparticles and sCT) obtained in Example 3 was administered. The effect enhanced by the invention nanoparticle preparation persisted until 8 hours had passed after administration.

Thus, it was confirmed that the nanoparticle preparation making use of the graft copolymer of the present invention improves gastrointestinal absorption of sCT.

Example 5

Preparation of a complex of nanoparticles and opioid peptide (OP) (a nanoparticle preparation of OP)

An aqueous opioid peptide solution having a concentration of 200 pg/ml and a dispersion (dispersion medium: water) of the nanoparticles obtained in Step 1-3 of Reference Example 1 (graft copolymer (A-1)), which had a concentration of 20 mg/ml, were independently prepared. The two were mixed in equal amounts and the nanoparticles were dispersed uniformly, to thereby obtain a nanoparticle preparation (a complex of nanoparticles and opioid peptide). Separately, an aqueous opioid peptide solution in which nanoparticles were not dispersed was prepared in a manner similar to that described above, to thereby obtain a control preparation (100 pg/ml opioid peptide). The chemical structure of the opioid peptide used in this Example is as follows:

$H_3CC(NH)$-Tyr-D-Arg-Phe-$N(CH_3)$-β-Ala

Example 6

In vivo evaluation of the complex of nanoparticles and opioid peptide (OP)

6-1. Method

To each of ddy male mice (3–4 weeks old, about 20–25 g) that were freely fed was administered perorally the nanoparticle preparation prepared in Example 5 or the control preparation (opioid pepetide: 1 mg/10 ml/kg). Pressure stimulus was applied to the basal part of the mouse's tail by use of a Randall & Selitto pressure-imparting apparatus (model MK-300, Muromachi Kikai), (32 g/second). Pain threshold values (g) were measured at several points of time (1, 2, 3, 4, 5, 6, 8, and 24 hrs.) by use of struggling, biting of the stimulated part, and similar behaviors as indices. The cut-off value was 500 g. The pain-related activity (% of MPE (maximum possible effect) was calculated according to the following equation:

% of MPE={(Pain threshold value after administration)−(Pain threshold value before administration)/(500−Pain threshold value before administration)}×100

6-2. Results

Figure 8:
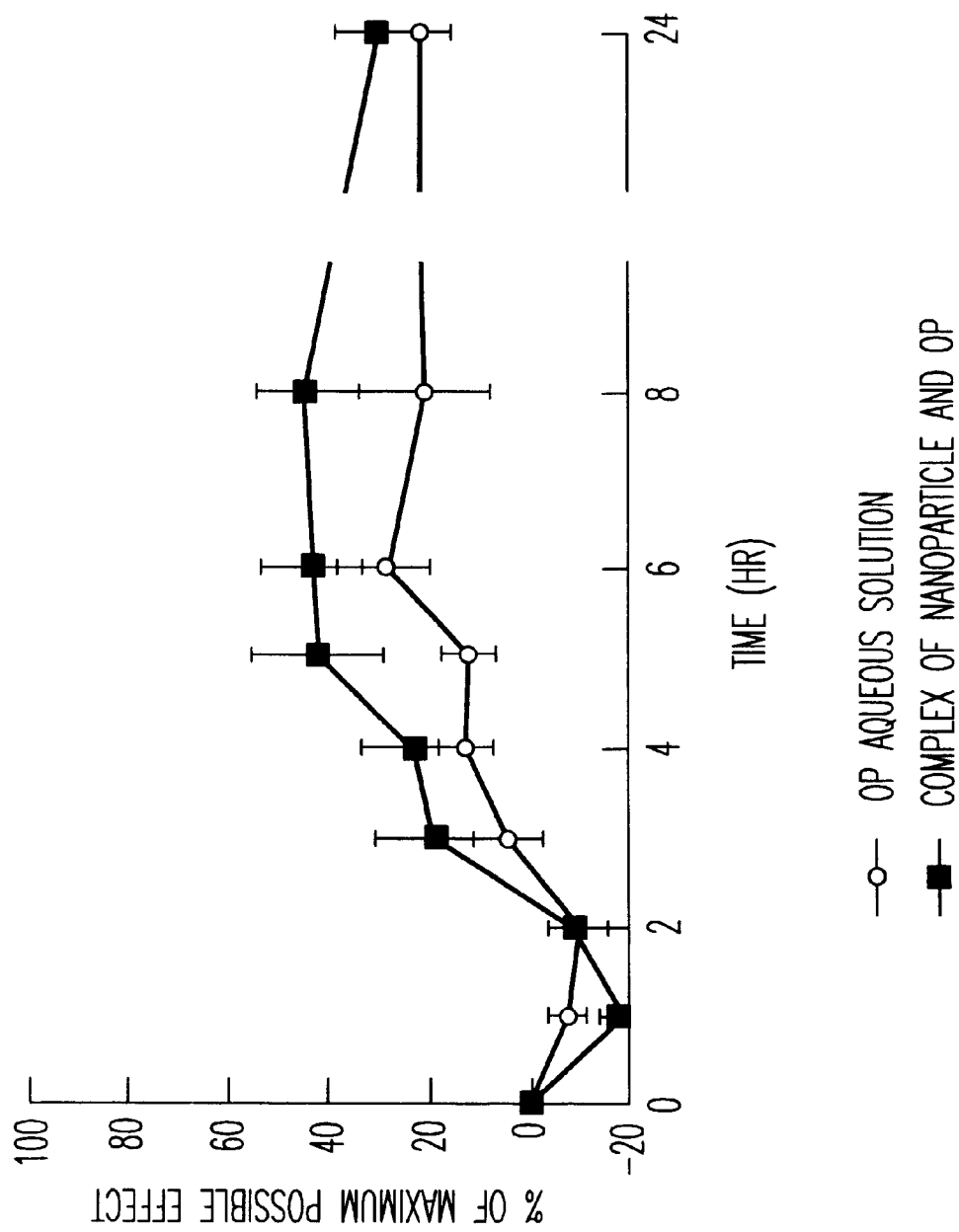
FIG. 8 is a graph showing the change of analgetic effect (mean±S.E.) with the passage of time when opioid peptide was perorally administered to mice in Example 6.

The results are shown in FIG. 8. As is apparent from FIG. 8, the pain-related activity (% of MPE) was confirmed to be enhanced by mixing the opioid peptide with nanoparticles.

Thus, it was confirmed that the nanoparticle preparation (a complex of nanoparticles and opioid peptide) making use of the graft copolymer of the present invention improves gastrointestinal absorption of opioid peptide.

Example 7

Preparation of a complex of nanoparticles and salmon calcitonin (sCT)

An aqueous sCT solution having a concentration of 200 µg/ml and a dispersion (dispersion medium: water) of the nanoparticles obtained in Reference Examples 2 and 4 (graft copolymers (A-2) and (A-4)), which had a concentration of 20 mg/ml, were independently prepared. The two were mixed in equal amounts and the nanoparticles were dispersed uniformly, to thereby obtain a nanoparticle preparation. Separately, an aqueous sCT solution in which nanoparticles were not dispersed was prepared in a manner similar to that described above, to thereby obtain a control preparation.

Example 8

In vivo evaluation of the complex of nanoparticles and salmon calcitonin (sCT)

By use of the nanoparticle preparation or the control preparation obtained in Example 7, the procedure of Example 4 was repeated to thereby determine the presence or absence of the effect of absorption enhancement obtained by the formation of nanoparticles. The results are shown in FIG. 9.

Figure 9:
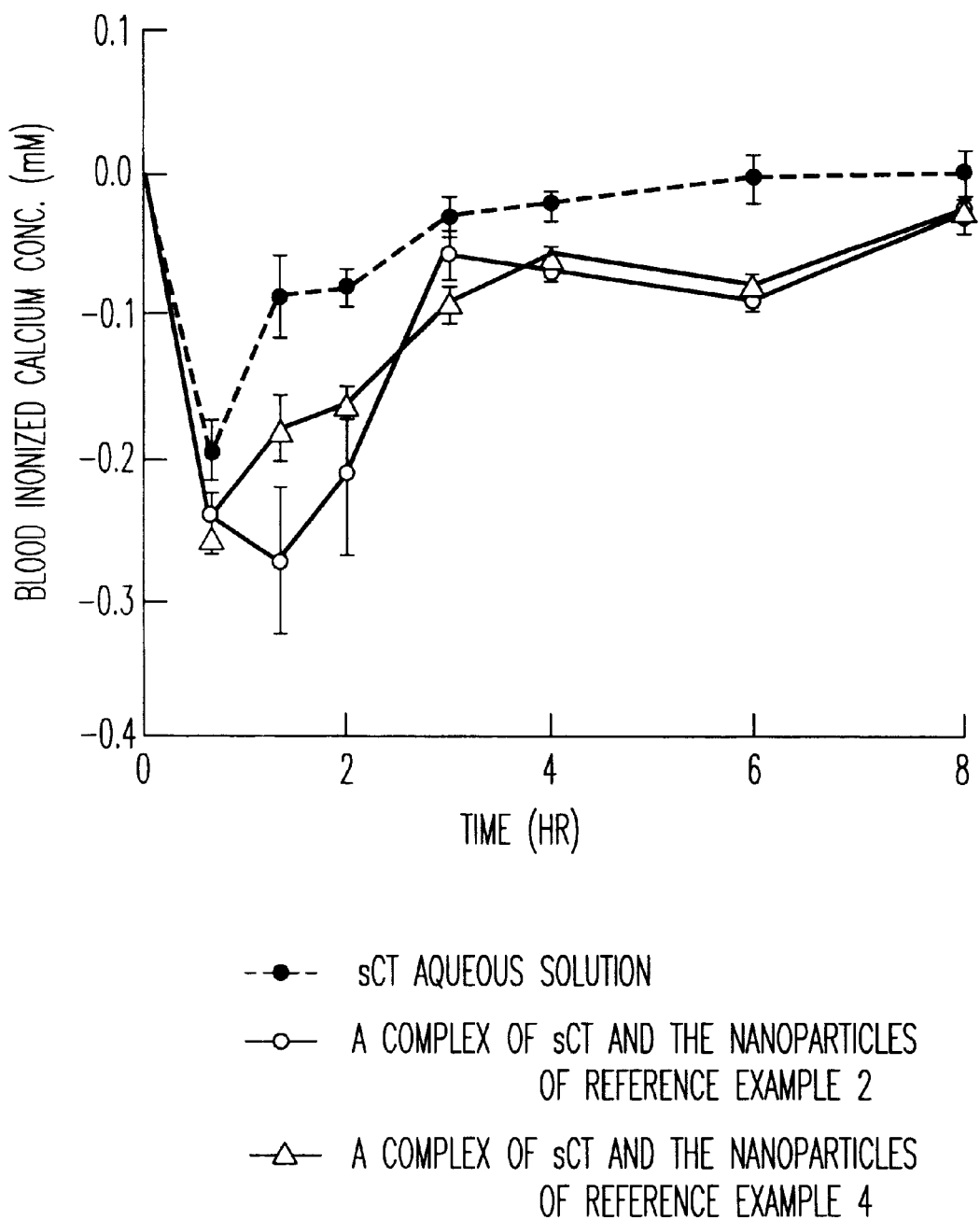
FIG. 9 is a graph showing the change of ionized calcium concentration in blood (mean±S.E.) as a function of time, after salmon calcitonin was perorally administered to rats in Example 8.

As is apparent from FIG. 9, the blood ionized calcium concentration was slightly decreased when the aqueous sCT solution (i.e., a control preparation) was administered, however this effect of reducing the blood ionized calcium concentration was considerably enhanced when the nanoparticle preparation (a complex of nanoparticles and sCT) obtained in Example 7 was administered. The effect enhanced by the invention nanoparticle preparation persisted until 6 hours had passed after administration.

Thus, it was confirmed that the nanoparticle preparation making use of the graft copolymer of the present invention improves gastrointestinal absorption of sCT.

Example 9

Preparation of a complex (which is a nanoparticle preparation) of a mixture of two different nanoparticles and salmon calcitonin (sCT)

An aqueous sCT solution having a concentration of 0.1 mg/ml, a dispersion (dispersion medium: water) of the nanoparticles obtained in Step 1-3 of Reference Example 1 (graft copolymer (A-1)), which had a concentration of 5 mg/ml, and a dispersion (dispersion medium: water) of the nanoparticles obtained in Reference Example 11 (graft copolymer (B-2-2)), which had a concentration of 5 mg/ml were independently prepared. The three were mixed in equal amounts and the nanoparticles were dispersed uniformly, to thereby obtain a nanoparticle preparation. Separately, an aqueous sCT solution in which nanoparticles were not dispersed was prepared in a manner similar to that described above, to thereby obtain a control preparation.

Example 10

In vivo evaluation of the mixture of nanoparticles and salmon calcitonin (sCT)

By use of the nanoparticle preparation or the control preparation obtained in Example 9, the procedure of Example 4 was repeated to thereby determine the presence or absence of the-effect of absorption enhancement obtained by the formation of nanoparticles. The results are shown in FIG. 10.

Figure 10:
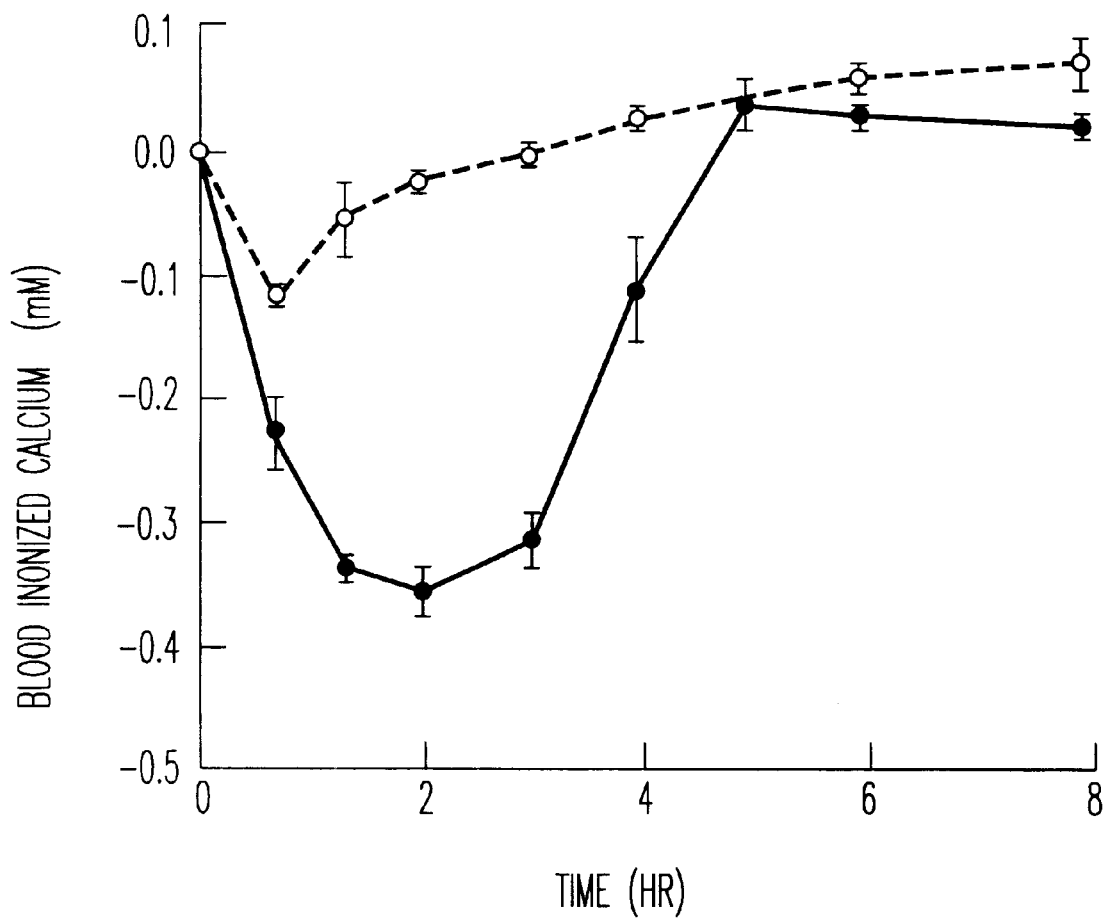
FIG. 10 is a graph showing the change of ionized calcium concentration in blood (mean±S.E.) as a function of time, after salmon calcitonin was perorally administered to rats in Example 10.

As is apparent from FIG. 10, the blood ionized calcium concentration was slightly decreased when the aqueous sCT solution (i.e., a control preparation) was administered, however this effect of reducing the blood ionized calcium concentration was considerably enhanced when the nanoparticle preparation (a complex of two different kinds of nanoparticles and sCT) obtained in Example 9 was administered. The effect enhanced by the invention nanoparticle preparation persisted until 5 hours had passed after administration. Moreover, the effect was even further enhanced as compared to the case in which a single kind of nanoparticles was used.

Thus, it was determined that the nanoparticle preparation making use of two or more kinds of the graft copolymer of the present invention improves gastrointestinal absorption of sCT.

Example 11

Divided administration of a nanoparticle preparation

A test was performed to investigate the absorption enhancement effect attained by a nanoparticle preparation when administered twice in divided amounts, with a time interval of 40 minutes.

An aqueous sCT solution having a concentration of 100 µg/ml and a dispersion (dispersion medium: water) of the nanoparticles obtained in Step 1-3 of Reference Example 1 (graft copolymer (A-1)), which dispersion had a concentration of 10 mg/ml, were independently prepared. The two were mixed in equal amounts and the nanoparticles were dispersed uniformly, to thereby obtain a nanoparticle preparation. Separately, an aqueous sCT solution in which nanoparticles were not dispersed was prepared in a manner similar to that described above, to thereby obtain a control preparation.

The procedure of Example 4 was repeated except that each preparation (0.5 ml) was divided into two (0.25 ml×2) and the divided portions were administered at time 0 and at 40 minutes, to thereby investigate the absorption enhancement effect of salmon calcitonin.

Figure 11:
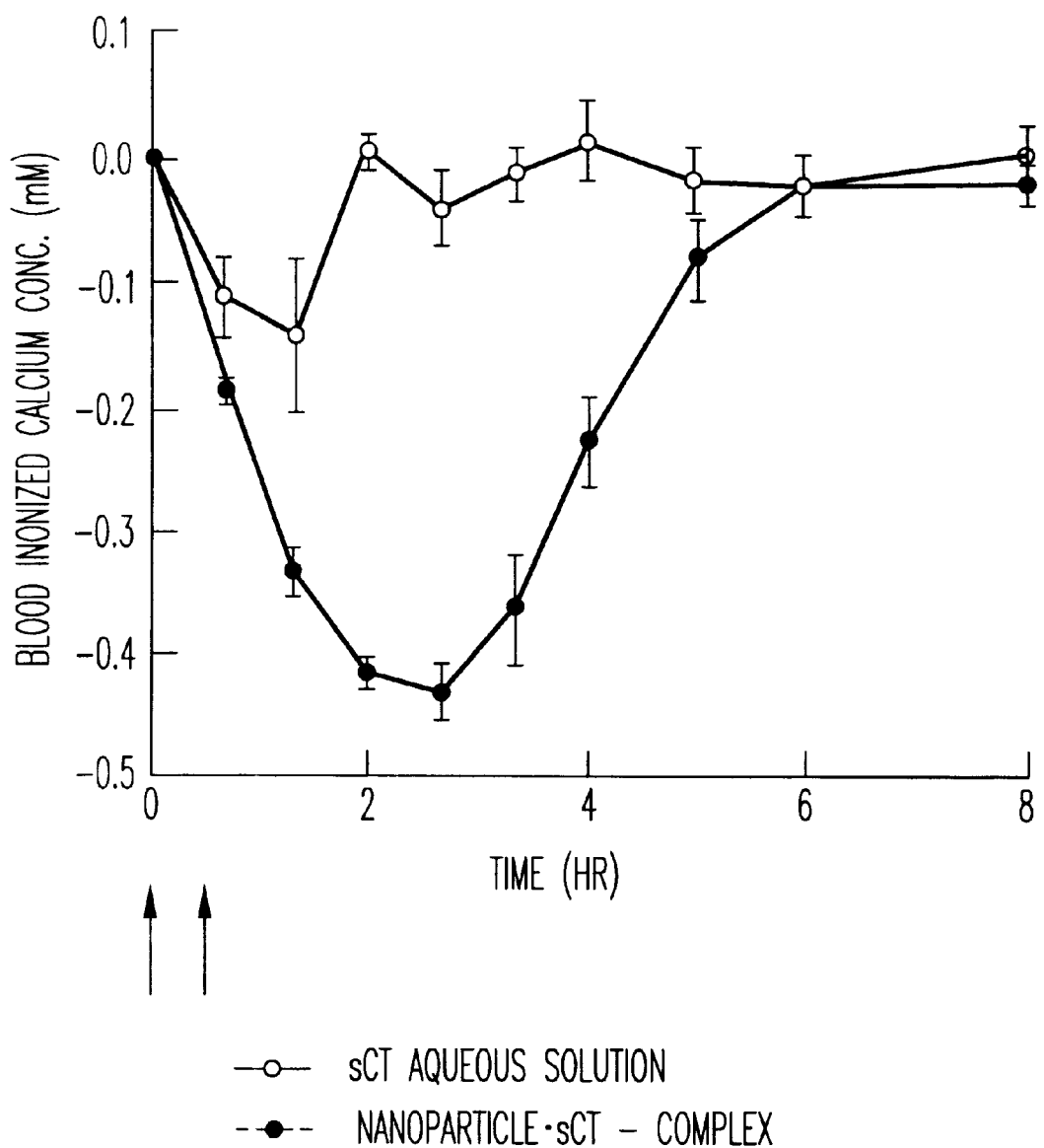
FIG. 11 is a graph showing the change of ionized calcium concentration in blood (mean±S.E.) as a function of time, after salmon calcitonin was perorally administered in divided portions to rats in Example 11.

As a result, as is apparent from FIG. 11, it was confirmed that the nanoparticle preparation of the present invention exerted an even improved effect of enhancing sCT absorption, when administered in divided amounts with a certain time interval.

Industrial Applicability

The pharmaceutical composition of the present invention that makes use of the particulate carriers exhibits an excellent peroral absorption enhancement effect of the drug incorporated in the composition. Therefore, it is particularly useful as a DDS for poor absorptive drugs.

What is claimed is:

1. A particulate carrier comprising a graft copolymer (A) consisting essentially of structural units of the following formulae (1) and (2):

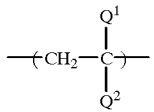

(1)

wherein $Q^1$ is a hydrogen atom, a methyl group, or a cyano group, and $Q^2$ is a hydrogen atom,

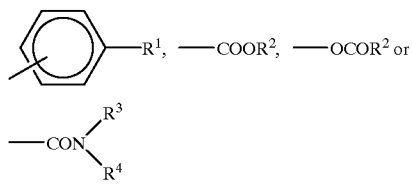

wherein $R^1$ is a hydrogen atom or a halogenomethyl group, $R^2$ is a $C_1$–$C_{10}$ alkyl group, $R^3$ is a hydrogen atom or a $C_1$–$C_{10}$ alkyl group, and $R^4$ is a $C_1$–$C_{10}$ alkyl group, provided that the total carbon number of $R^3$ and $R^4$ taken together is between 3 and 20 inclusive;

(2)

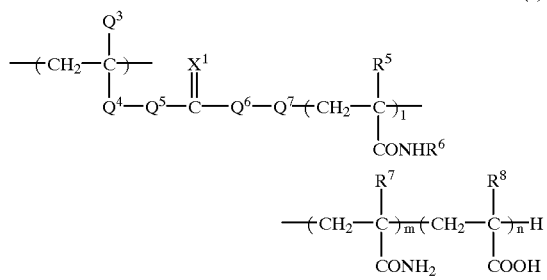

wherein $Q^3$ is a hydrogen atom or a methyl group, $Q^4$ is a group having the following structure:

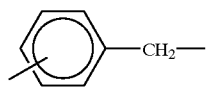

wherein $A^1$ is a $C_1$–$C_{10}$ alkylene group, $Q^5$ is an oxygen atom, $Q^6$ is a $C_1$–$C_{10}$ alkylene group, $Q^7$ is an oxygen atom or a sulfur atom, $X^1$ is two hydrogen atoms, each of $R^5$, $R^7$, and $R^8$ is a hydrogen atom or a methyl group, $R^6$ is a $C_1$–$C_{10}$ alkyl group, l is a number from 1 to 100, and each of m and n is a number from 0 to 100;

wherein the mole fraction of the structural unit of formula (2) in graft copolymer (A) is between 0.001 and 1.

2. A particulate carrier composition comprising the following components (a) and (b):

(a) the graft copolymer (A) as defined in claim 1; and (b) one or more graft copolymers selected from the group consisting of the following graft copolymers (B-1) and (B-2):

(B-1) a graft copolymer consisting essentially of structural units of the following formulae (1) and (3):

(1)

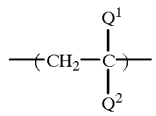

wherein $Q^1$ is a hydrogen atom, a methyl group, or a cyano group, and $Q^2$ is a hydrogen atom,

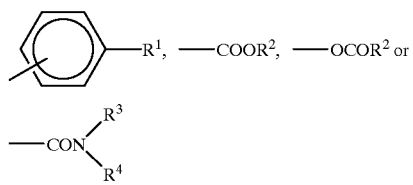

wherein $R^1$ is a hydrogen atom or a halogenomethyl group, $R^2$ is a $C_1$–$C_{10}$ alkyl group, $R^3$ is a hydrogen atom or a $C_1$–$C_{10}$ alkyl group, and $R^4$ is a $C_1$–$C_{10}$ alkyl group, provided that the total carbon number of $R^3$ and $R^4$ taken together is between 3 and 20 inclusive;

(3)

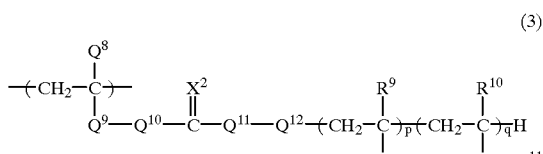

wherein $Q^8$ is a hydrogen atom or a methyl group, $Q^9$ is a group having the following structure:

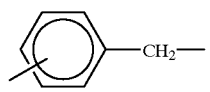

wherein $A^2$ is a $C_1$–$C_{10}$ alkylene group, $Q^{10}$ is an oxygen atom, $Q^{11}$ is a $C_1$–$C_{10}$ alkylene group, $Q^{12}$ is an oxygen atom or a sulfur atom, $X^2$ is two hydrogen atoms, each of $R^9$ and $R^{10}$ is a hydrogen atom or a methyl group, $R^{11}$ is a $C_1$–$C_{10}$ alkyl group, and p and q are independently numbers from 0 to 100 such that the sum p+q is greater than or equal to 1;

(B-2) a graft copolymer consisting essentially of structural units of the following formulae (1) and (4):

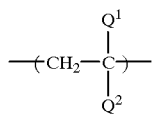
(1)

wherein $Q^1$ is a hydrogen atom, a methyl group, or a cyano group, and $Q^2$ is a hydrogen atom,

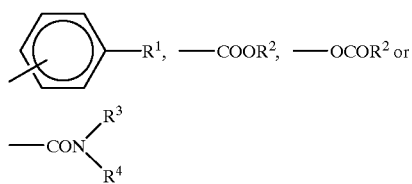

wherein $R^1$ is a hydrogen atom or a halogenomethyl group, $R^2$ is a $C_1$–$C_{10}$ alkyl group, $R^3$ is a hydrogen atom or a $C_1$–$C_{10}$ alkyl group, and $R^4$ is a $C_1$–$C_{10}$ alkyl group, provided that the total carbon number of $R^3$ and $R^4$ taken together is between 3 and 20 inclusive;

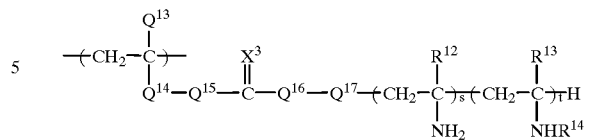
(4)

wherein $Q^{13}$ is a hydrogen atom or a methyl group, $Q^{14}$ is a group having the following structure:

wherein $A^3$ is a $C_1$–$C_{10}$ alkylene group, $Q^{15}$ is an oxygen atom, $Q^{16}$ is a $C_1$–$C_{10}$ alkylene group, $Q^{17}$ is an oxygen atom or a sulfur atom, $X^3$ is two hydrogen atoms, each of $R^{12}$ and $R^{13}$ is a hydrogen atom or a methyl group, $R^{14}$ is a $C_2$–$C_{11}$ alkanoyl group, and m and t are independently numbers from 0 to 100 such that the sum s+t is greater than or equal to 1;

and wherein:

the mole fraction of the structural unit of formula (2) in graft copolymer (A) is between 0.001 and 1, the mole fraction of the structural unit of formula (3) in graft copolymer (B-1) is between 0.001 and 1, and the mole fraction of the structural unit of formula (4) in graft copolymer (B-2) is between 0.001 and 1.

\* \* \* \* \*

UNITED STATES PATENT AND TRADEMARK OFFICE
CERTIFICATE OF CORRECTION

PATENT NO. : 6,100,338
DATED : August 8, 2000
INVENTOR(S): Mitsuru AKASHI et al

It is certified that an error appears in the above-identified patent and that said Letters Patent is hereby corrected as shown below:

Column 32, line 22, Claim 2, "ato ms" should read --atoms--.
Column 32, line 24, Claim 2, "m and t" should read --s and t--.

Signed and Sealed this

First Day of May, 2001

Attest:

NICHOLAS P. GODICI

Attesting Officer   Acting Director of the United States Patent and Trademark Office